United States Patent
Breitler et al.

(10) Patent No.: US 12,139,506 B2
(45) Date of Patent: Nov. 12, 2024

(54) PROCESS FOR THE PREPARATION OF GALNAC PHOSPHORAMIDITE EPIMERS

(71) Applicant: Hoffmann-La Roche Inc., Little Falls, NJ (US)

(72) Inventors: Simon Adolf Breitler, Basel (CH); Kurt Puentener, Erstfeld (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 601 days.

(21) Appl. No.: 17/612,900

(22) PCT Filed: May 18, 2020

(86) PCT No.: PCT/EP2020/063749
§ 371 (c)(1),
(2) Date: Nov. 19, 2021

(87) PCT Pub. No.: WO2020/234208
PCT Pub. Date: Nov. 26, 2020

(65) Prior Publication Data
US 2022/0259248 A1    Aug. 18, 2022

(30) Foreign Application Priority Data
May 20, 2019  (EP) .................................... 19175309

(51) Int. Cl.
| C07H 15/08 | (2006.01) |
| C07H 1/00  | (2006.01) |
| C07H 21/00 | (2006.01) |

(52) U.S. Cl.
CPC .............. C07H 15/08 (2013.01); C07H 1/00 (2013.01); C07H 21/00 (2013.01)

(58) Field of Classification Search
None
See application file for complete search history.

(56) References Cited

FOREIGN PATENT DOCUMENTS

| WO | 2017/084987 A1 | 5/2017 |
| WO | 2018/215391 A1 | 11/2018 |

OTHER PUBLICATIONS

Cedillo et al., "Synthesis of 5'-GalNAc-Conjugated Oligonucleotides: A Comparison of Solid and Solution-Phase Conjugation Strategies" Molecules 22(8):1356, 1-12 (Aug. 15, 2017).
International Preliminary Report on Patentability for PCT/EP2020/063749 issued Nov. 16, 2021.
International Search Report for PCT/EP2020/063749 mailed Jul. 16, 2020.

*Primary Examiner* — Layla D Berry

(57) ABSTRACT

The invention comprises a process for the preparation of a GalNAc phosphoramidite epimer of the formula (I), wherein $R^1$ is a hydroxy protecting group, n is an integer from 0 to 10 and m is an integer from 0 to 20, corresponding enantiomers and/or optical isomers thereof and the use of the process for the preparation of GalNAc-cluster oligonucleotide conjugates.

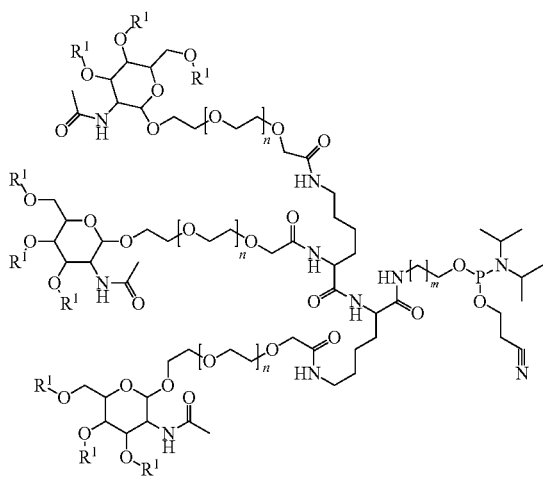

21 Claims, No Drawings
Specification includes a Sequence Listing.

PROCESS FOR THE PREPARATION OF GALNAC PHOSPHORAMIDITE EPIMERS

The invention relates to a novel process for the preparation of epimerically pure GalNAc phosphoramidite epimers of the formula I,

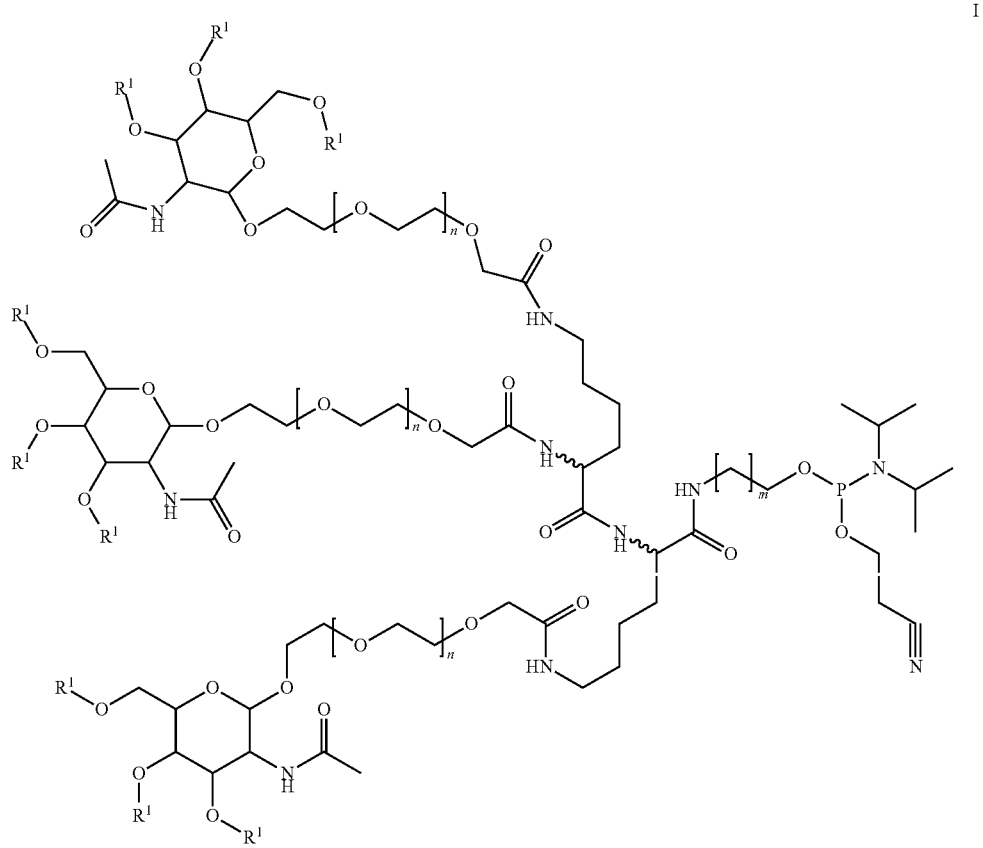

wherein $R^1$ is a hydroxy protecting group, n is an integer from 0 to 10 and m is an integer from 0 to 20, corresponding enantiomers and/or optical isomers thereof.

GalNAc phosphoramidites of formula I carry the GalNAc moiety which is the targeting moiety of conjugates comprising the GalNAc moiety. The GalNAc moiety, due to its affinity to the asialoglycoprotein receptor, which is located on the liver cell enables functional delivery of oligonucleotide conjugates to the liver cell. Such GalNAc cluster conjugates have the potential to act as pharmacokinetic modulators and therefore be therapeutically valuable compounds as e.g. described in the PCT Publication WO 2017/084987.

Due to the unique combination of GalNAc moiety and phosphoramidite the GalNAc phosphoramidite of formula I can directly be introduced as building block together with the nucleoside building blocks in the solid phase oligonucleotide synthesis. A separate conjugation step to introduce the GalNAc moiety can therefore be avoided.

According to the current process described in the PCT Publication WO 2017/084987 GalNAc phosphoramidites of the formula I, can be prepared by a) the reaction of a GalNAc acid derivative of formula A

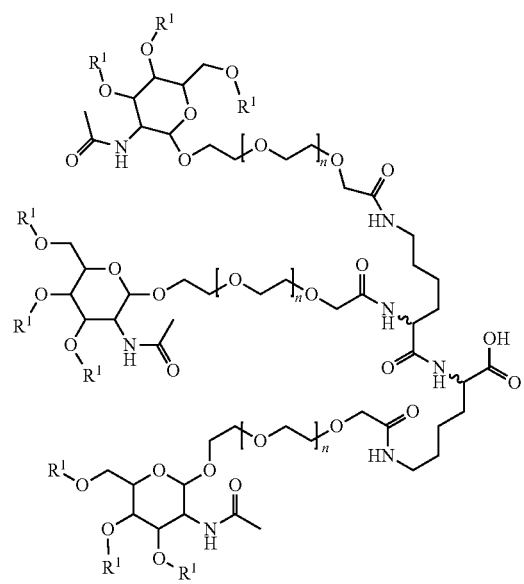

wherein $R^1$ is a hydroxy protecting group and n is an integer from 0 to 10, with an amine of formula IV

B

H₂N—(—)ₘ—O—R³ wherein $R^3$ is a hydroxy protecting group and m is an integer from 0 to 20 to form an amide of formula C b) removal of the hydroxy protecting group $R^3$ to form the GalNAc amide of formula D

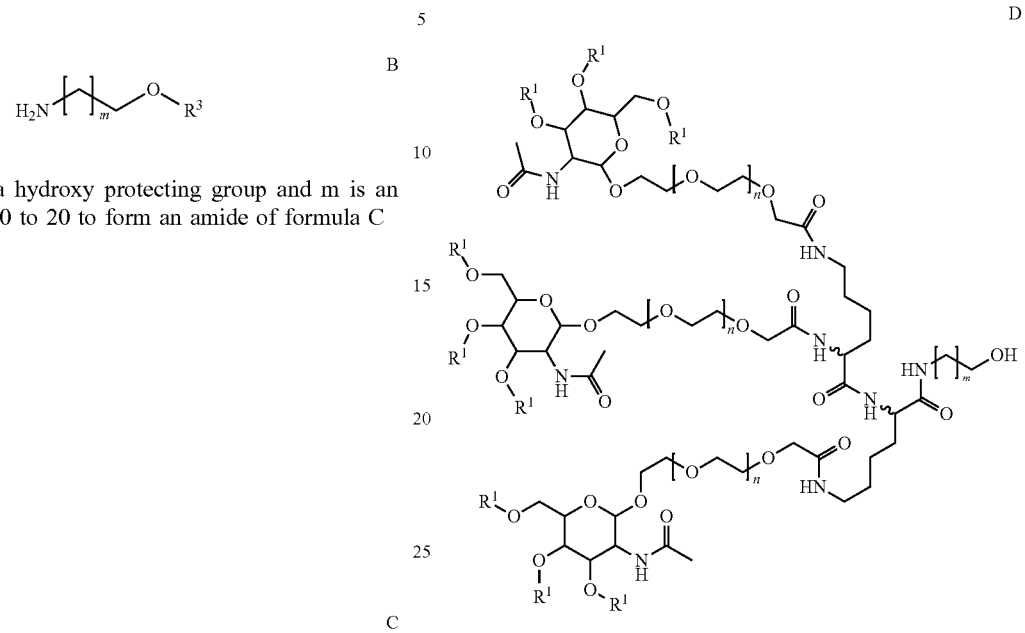

wherein IV, n and m are as above and c) the reaction of the GalNAc amide of formula D with a phosphoroamidating agent to form the GalNAc phosphoramidite derivative of the formula I.

It was found that this process leads to racemization at the designated chiral center (arrow in formula I below) in the coupling step a)

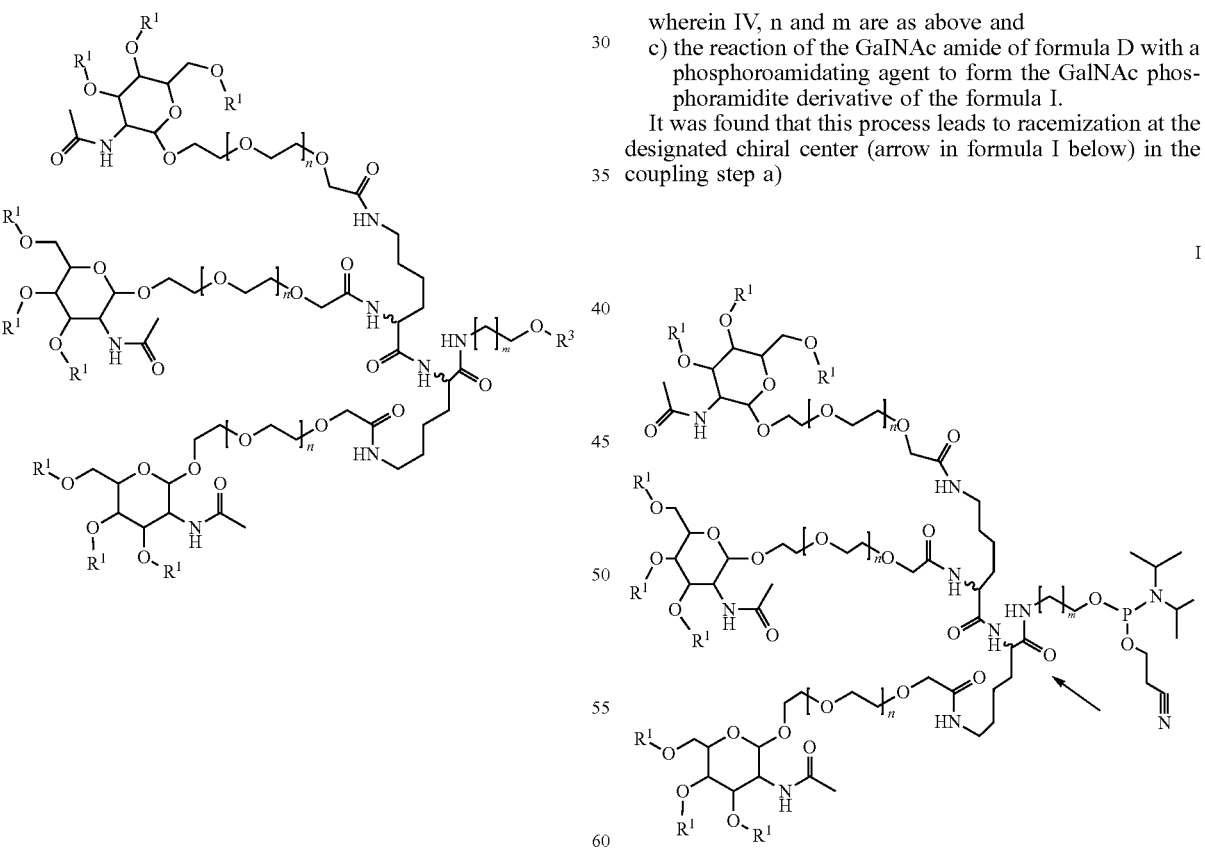

wherein $R^1$, $R^3$, n and m are as above;

The object of the invention therefore was to provide a novel process to produce the building block in epimerically pure form.

The object could be achieved with the novel process for the preparation of epimerically pure GalNAc phosphoramidite epimers of the formula I which comprises a) coupling a compound of formula II,
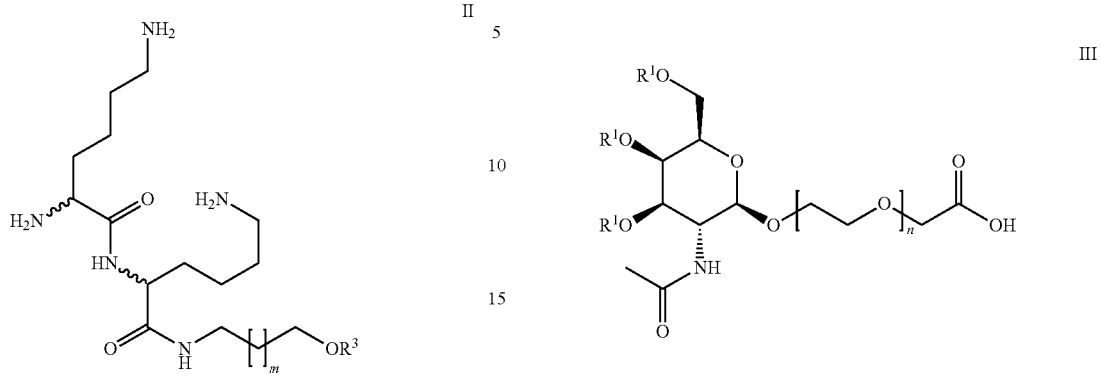
with a GalNAc moiety of the formula III
wherein $R^3$ is a hydroxy protecting groups and m is as above, or a salt thereof
wherein $R^1$ and n is as above to form the GalNAc amide of formula IV
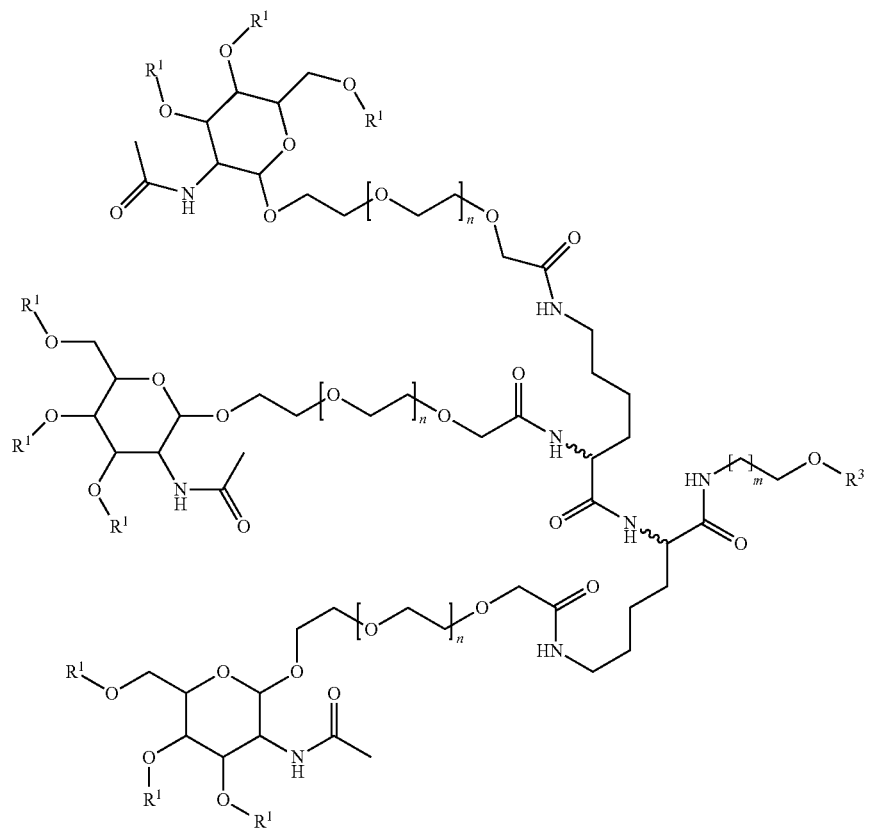

wherein $R^1$, $R^3$, n and m are as above; and b) removing the hydroxyl protecting group $R^3$ to form the free alcohol GalNAc amide of formula IV and c) reacting the free alcohol of the GalNAc amide of formula IV with a phosphoroamidating agent to form the GalNAc phosphoramidite epimer of the formula I The following definitions are set forth to illustrate and define the meaning and scope of the various terms used to describe the invention herein.

Whenever a chiral carbon is present in a chemical structure, it is intended that all stereoisomers associated with that chiral carbon are encompassed by the structure as pure stereoisomers as well as mixtures thereof.

The term epimer denotes one of a pair of stereoisomers, wherein the isomers differ in configuration at only one stereogenic center and wherein all other stereocenters in the molecules are the same.

The term "$C_{1-12}$-alkyl" denotes a monovalent linear or branched saturated hydrocarbon group of 1 to 12 carbon atoms and the term "$C_{1-6}$-alkyl" a monovalent linear or branched saturated hydrocarbon group of 1 to 6 carbon atoms.

Examples of "$C_{1-12}$-alkyl" or "$C_{1-6}$-alkyl" include methyl, ethyl, propyl, isopropyl, n-butyl, iso-butyl, sec-butyl, tert-butyl, and pentyl and hexyl with its isomers.

The term "acyl" denotes a carbonyl group which is linked to an alkyl group. The term particularly stands for a $C_{1-12}$-alkylcarbonyl group, more particularly a $C_{1-6}$-alkylcarbonyl group which is optionally substituted by $C_{1-6}$-alkyl or optionally substituted by phenyl. Examples for acyl groups are acetyl, pivaloyl or benzoyl. Optional substitutions for phenyl are halogen such as chlorine, bromine or iodine or a $C_{1-6}$-alkyl group as defined above. Acyl preferably stands for acetyl.

The term "hydroxy-protecting group" denote groups which are intended to protect a hydroxy group and include ester- and ether-forming groups, in particular tetrahydropyranyl, acyl (e.g. benzoyl, acetyl, carbamoyl), benzyl and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, NY, 1991, chapters 2-3; E. Haslam, "Protective Groups in Organic Chemistry", J. G. W. McOmie, Ed., Plenum Press, New York, NY, 1973, Chapter 5, and T. W. Greene, "Protective Groups in Organic Synthesis", John Wiley and Sons, New York, NY, 1981.

The term "amino-protecting group" denotes groups intended to protect an amino group and includes benzoyl, benzyloxycarbonyl, carbobenzyloxy (CBZ or Z), 9-fluorenylmethyloxycarbonyl (FMOC), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, NY, 1991, chapter 7; E. Haslam, "Protective Groups in Organic Chemistry", J. G. W. McOmie, Ed., Plenum Press, New York, NY, 1973, Chapter 5, and T. W. Greene, "Protective Groups in Organic Synthesis", John Wiley and Sons, New York, NY, 1981.

GalNAc phosphoramidite epimers of the formula I are preferably those wherein $R^1$ is a $C_{1-6}$-alkylcarbonyl group which is optionally substituted by $C_{1-6}$-alkyl or phenyl, n is an integer from 0 to 5 and m is an integer from 0 to 10, more preferably those wherein $R^1$ is acetyl, n is 2 and m is 5.

In a more preferred embodiment, the GalNAc phosphoramidite epimers of the formula I comprise the compounds of the formulas Ib to Ie.

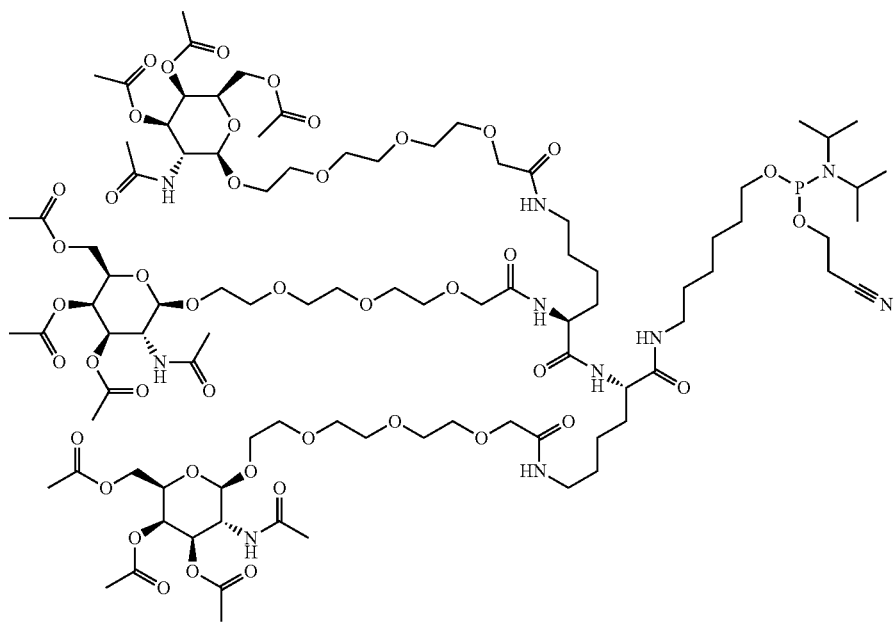

Ib

Ic
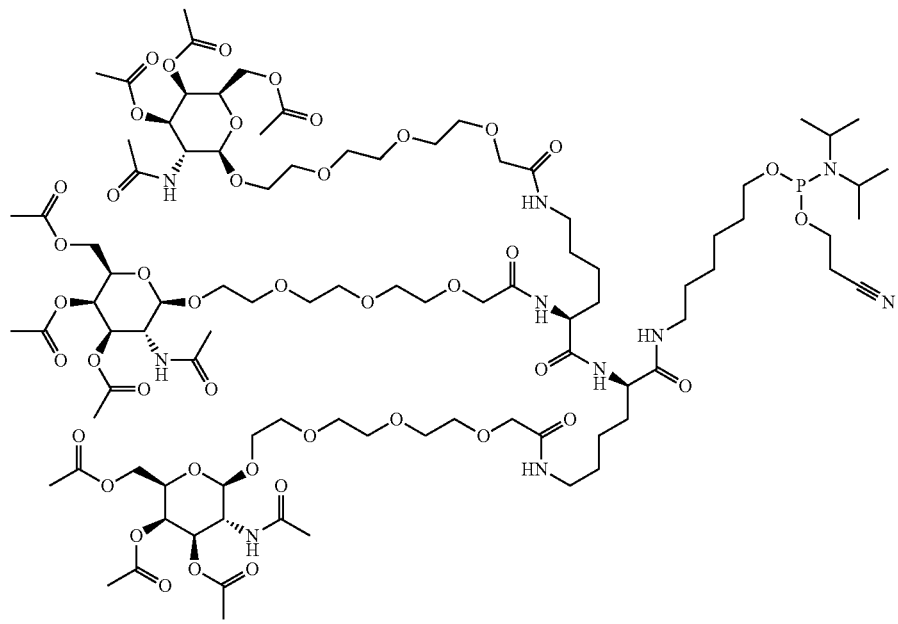
Id
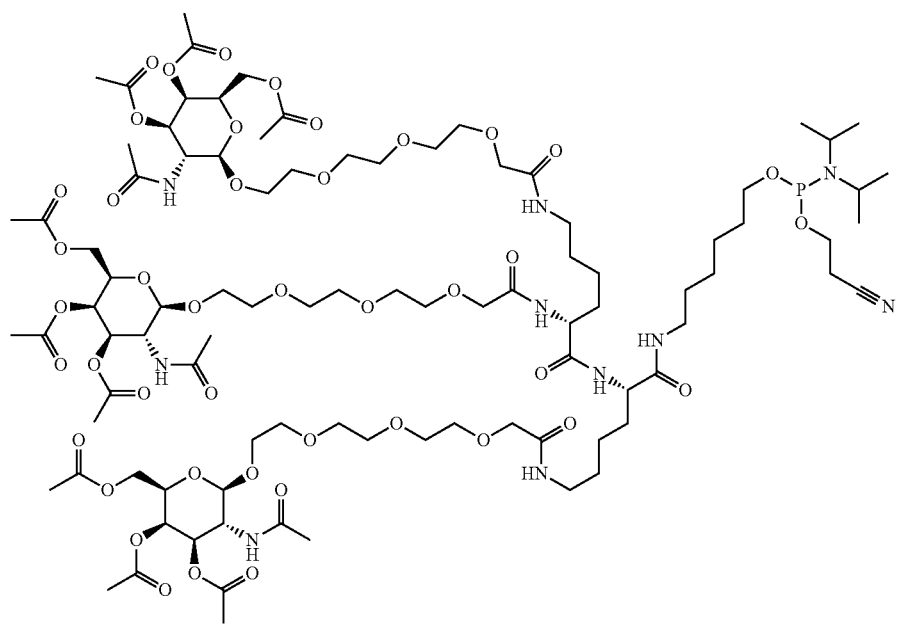

-continued

Ie

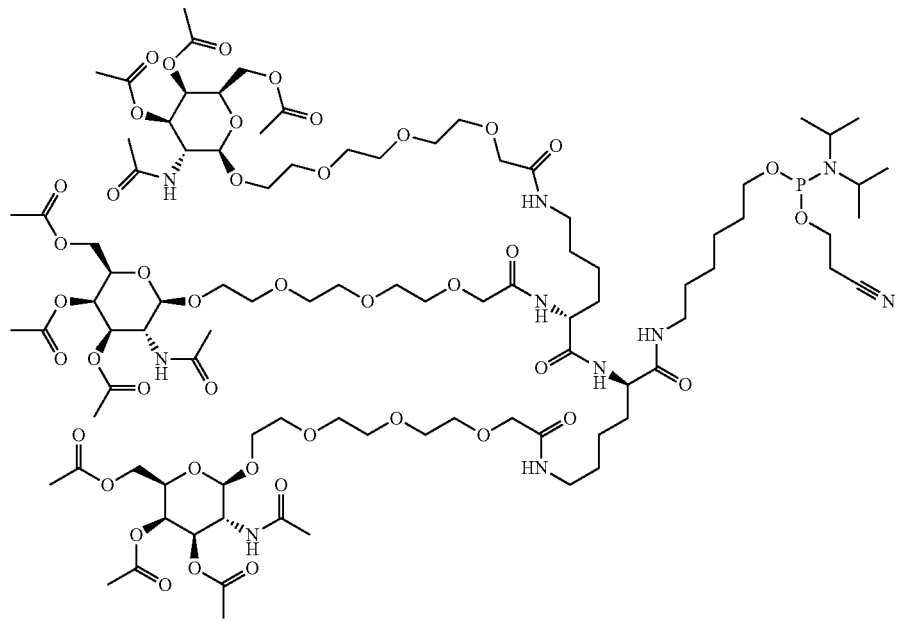

Even more preferred are the epimers of formula Ib and Ic.

Step a)

Step a) is characterized by the coupling of a compound of formula II or of a salt thereof with a GalNAc moiety of the formula III to form the GalNAc amide of formula IV.

The compound of formula II or the salt thereof can be prepared by a1) coupling a lysine compound of formula V

V

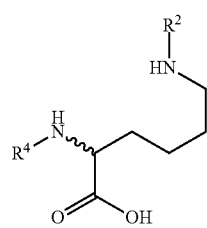

wherein $R^2$ and $R^4$ are amino protecting groups, with an amine of the formula VI

VI

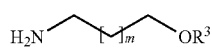

wherein $R^3$ is a hydroxyl protecting group and m is as above to form the carboxamide of formula VII;

VII

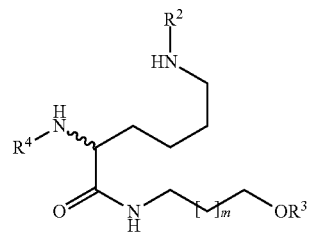

wherein $R^2$, $R^3$, $R^4$ and m are as above and by b1) removing the amino protecting group $R^4$ to form the amine of formula VIII

VIII

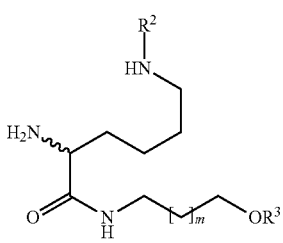

wherein $R^2$ and $R^3$ and m are as above;

c1) coupling the amine of formula VIII with an amino group protected lysine to form the dipeptide of formula IX

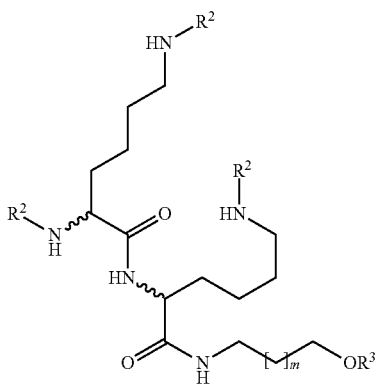

IX wherein $R^2$ and $R^3$ and m are as above; and d1) removing the amino protecting groups $R^2$ to form the compound of formula II.

In a preferred embodiment the coupling steps a1) and c1) are performed in the presence of a peptide coupling agent, an amine base and an organic solvent.

The coupling can follow the classical methods known to the skilled in the art using a carbodiimide coupling agent like DCC (N,N'-Dicyclohexylcarbodiimide) or EDC (N-(N'',N''-dimethylaminopropyl-N'-ethylcarbodiimide) with or without an additive like HOBt (1-hydroxybenztriazole) or HOSu (N-hydroxysuccinimide), TBTU (N,N,N',N'-Tetramethyl-O-(benzotriazol-1-yl)uronium tetrafluoroborate, HBTU (2-(1H-benzotriazol-1-yl)-1,1,3,3-tetramethyluronium hexafluorophosphate) or HOAt (1-Hydroxy-7-azabenzotriazole and common combination thereof such as TBTU/HOBt or HBTU/HOAt.

In a preferred embodiment n-propylphosphonic acid anhydride (T3P) is selected as coupling agent together with a tertiary amine as amine base, like triethylamine, N-methylmorpholine or N-diisopropylethylamine, but preferably with N-diisopropylethylamine.

The coupling reactions usually takes place in a polar aprotic solvent like acetonitrile, ethyl acetate or tetrahydrofuran or mixtures thereof at reaction temperatures in the range of 20° C. and 70° C., preferably in the range of 20° C. and 40° C.

The products from the coupling steps a1) and c1) can be obtained from the organic layer of the reaction mixture applying methods known to the skilled in the art for instance by a washing of the organic phase and subsequent removal of the solvent by evaporation.

The amino protecting group $R^4$ typically is an amino protecting group which is cleavable under basic conditions. FMOC is the most preferred amino protecting group. The basic conditions as a rule involve the treatment with a secondary aliphatic amine, such as with piperidine, 4-methylpiperidine, pyrrolidine or diethyl amine, but preferably with diethyl amine in the presence of an organic solvent. Suitable solvents are polar aprotic solvent like acetonitrile or tetrahydrofuran or mixtures thereof.

The amino protecting group $R^2$ typically is an amino protecting group which is cleavable under acidic conditions, preferably tert-butyloxycarbonyl (Boc).

The removal of the amino protecting group $R^2$ therefore can take place with suitable acids for instance selected form hydrochloric acid, trifluoro acetic acid, sulfonic acids such as p-toluene sulfonic acid or methanesulfonic acid in a polar aprotic solvent such as in acetonitrile.

In a preferred embodiment methanesulfonic acid is applied.

The acidic treatment forms the tri-ammonium salt of the dipeptide of formula IX with the respective acid, for the preferred embodiment to the tri-ammonium salt of the dipeptide of formula IX with methanesulfonic acid.

The tri-ammonium salt of the dipeptide of formula IX can be isolated by applying methods known to the skilled in the art, such as crystallization or is directly applied in the coupling with the GalNAc moiety of formula III in step b).

The GalNAc moiety of the formula III can be prepared in accordance with the disclosure in PCT Int. Publication WO 2017/084987, particularly in accordance with its example 7.

The final coupling of the compound of formula II or of a salt thereof, such as the tri-ammonium salt of the dipeptide of formula IX with the GalNAc moiety of the formula III can be performed under the coupling conditions mentioned above. Also, the preferred reaction conditions reported above can be applied for this coupling reaction.

The GalNAc amide of formula IV can be further purified by reverse phase chromatography and the product containing fractions can for instanced be lyophilized to obtain the purified GalNAc amide of formula IV Step b)

Step b) requires the removal of the hydroxyl protecting group $R^3$ to form the free alcohol of the GalNAc amide of formula IV.

It is important that the hydroxy protecting group $R^3$ is chemically different from the hydroxy protecting group $R^1$, such that removal conditions can be selected in a manner that the hydroxy protecting group $R^3$ is cleaved while the hydroxy protecting group $R^1$ remains unaffected.

A suitable hydroxy protecting group $R^3$ is benzyl which is optionally substituted by halogen or $C_{1-6}$-alkyl or is benzhydryl or trityl, i.e. a group which can be cleaved by hydrogenolysis.

In a preferred embodiment $R^3$ is benzyl and the hydrogenolysis is a catalytic hydrogenation with hydrogen in the presence of a suitable hydrogenation catalyst.

Suitable hydrogenation catalyst for the removal of the benzyl group is palladium on carbon (Pd/C).

The reaction is usually performed in the presence of polar protic solvents like an aliphatic alcohol such as 2-propanol or polar aprotic solvents such as THF or ethyl acetate at reaction temperatures between 0° C. and 40° C., preferably 10° C. and 30° C. and at a hydrogen pressure of 10 bar to 100 bar, preferably 30 bar to 80 bar.

The free alcohol of the GalNAc amide of formula IV can be obtained by filtering off the catalyst and concentration of the filtrate by evaporation in vacuo.

Step c)

Step c) requires reacting the free alcohol of the GalNAc acid amide of formula IV with a phosphoroamidating agent to form the GalNAc phosphoramidite epimer of the formula I.

The phosphoroamidating agent can be selected from 2-cyanoethyl-N,N-di-(2-propyl)chlorophosphoroamidite or from 2-Cyanoethyl-N,N,N',N'-tetra (2-propyl)phosphorodiamidite.

In a preferred embodiment the phosphoroamidating agent is 2-Cyanoethyl-N,N,N',N'-tetra (2-propyl)phosphorodiamidite combined with an activating agent.

The activating agents can be selected from an acidic ammonium salt of a secondary amine, preferably of a secondary aliphatic amine like diisopropylamine, preferably diisopropyl ammonium tetrazolide. Alternatively, other tetrazole type activating agents like tetrazole, 5-(ethylthio)-1H-tetrazole, 5-(benzylthio)-1H-tetrazole or 4,5-dicyanoimidazole may be used.

The reaction can be performed in polar aprotic solvents like dichloromethane, tetrahydrofuran or acetonitrile at a reaction temperature between −20° C. and 50° C., preferably between 10° C. and 30° C.

Isolation of the product from the reaction mixture can take place by evaporation. However, as a rule the product is left in solution and further purified by preparative chromatography.

Alternatively, the reaction mixture of the above described phosphoroamidating reaction can be used directly without chromatographic purification for the Solid Phase oligonucleotide synthesis.

In a preferred embodiment the chromatographically purified product GalNAc phosphoramidite epimer of the formula I is dissolved in a polar aprotic solvent such as dichloromethane or acetonitrile or mixtures thereof and directly applied for the preparation of GalNAc-cluster oligonucleotide conjugates. Alternatively, the product solutions can be dried over drying agents such as molecular sieves (3 Å or 4 Å), anhydrous $K_2CO_3$, basic activated alumina, $CaCl_2$ or $CaH_2$, preferably $CaH_2$ or 3 Å molecular sieves.

The preparation of GalNAc-cluster oligonucleotide conjugates comprises
a) the preparation of the GalNAc phosphoramidite epimer of the formula I;
b) the employment of the GalNAc phosphoramidite epimer of the formula I in a solid phase oligonucleotide synthesis together with a desired nucleoside building block in a desired sequence to form a desired GalNAc-cluster oligonucleotide conjugate bound to the solid support and finally the
c) cleavage of the GalNAc-cluster_oligonucleotide conjugate from the solid phase support and full deprotection and purification.

The term oligonucleotide as used herein is defined as it is generally understood by the skilled person as a molecule comprising two or more covalently linked nucleosides. For use as a therapeutically valuable oligonucleotide, oligonucleotides are typically synthesized as 7-30 nucleotides in length. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides or nucleotides. In some embodiments, the oligonucleotide is an antisense oligonucleotide.

The oligonucleotides may consist of DNA, RNA, modified RNA or LNA nucleoside monomers or combinations thereof. The LNA nucleoside monomers are modified nucleosides which comprise a linker group (referred to as a bi-radicle or a bridge) between C2' and C4' of the ribose sugar ring of a nucleotide. These nucleosides are also termed bridged nucleic acid or bicyclic nucleic acid (BNA) in the literature.

In a non-limiting embodiment, the GalNAc-cluster oligonucleotide conjugates may be selected from the group consisting of:

5'-(S,S)-GalNAc-C6-caG$_s^{Me}$C$_s$G$_s$t$_s$a$_s$a$_s$a$_s$g$_s$a$_s$g$_s$a$_s$G$_s$G-3'

5'-(S,S)-GalNAc-C6-caG$_s^{Me}$C$_s$G$_s$t$_s$a$_s$a$_s$a$_s$g$_s$a$_s$g$_s$a$_s$G$_s$G-3'

5'-(R,S)-GalNAc-C6-caG$_s^{Me}$C$_s$G$_s$t$_s$a$_s$a$_s$a$_s$g$_s$a$_s$g$_s$a$_s$G$_s$G-3'

5'-(S,S)-GalNAc-C6-
ca$^{Me}$C$_s^{Me}$C$_s$t$_s$a$_s$t$_s$t$_s$a$_s$a$_s$c$_s$a$_s$t$_s$c$_s$A$_s$G$_s$A$_s^{Me}$C-3'

5'-(R,S)-GalNAc-C6-
ca$^{Me}$C$_s^{Me}$C$_s$t$_s$a$_s$t$_s$t$_s$a$_s$a$_s$c$_s$a$_s$t$_s$c$_s$A$_s$G$_s$A$_s^{Me}$C-3'

5'-(S,S)-GalNAc-C6-
caT$_s^{Me}$C$_s$A$_s$a$_s$c$_s$t$_s$t$_s$t$_s$c$_s$a$_s$c$_s$t$_s$t$_s^{Me}$C$_s$A$_s$G$_s$-3'

5'-(R,S)-GalNAc-C6-
caT$_s^{Me}$C$_s$A$_s$a$_s$c$_s$t$_s$t$_s$t$_s$c$_s$a$_s$c$_s$t$_s$t$_s^{Me}$C$_s$A$_s$G$_s$-3'

5'-(S,S)-GalNAc-C6$_s$-A$_s$A$_s$T$_s$g$_s$c$_s$t$_s$a$_s$c$_s$a$_s$a$_s$a$_s$a$_s$c$_s^{Me}$C$_s^{Me}$C$_s$A-3'

5'-(R,S)-GalNAc-C6$_s$-A$_s$A$_s$T$_s$g$_s$c$_s$t$_s$a$_s$c$_s$a$_s$a$_s$a$_s$a$_s$c$_s^{Me}$C$_s^{Me}$C$_s$A-3' wherein uppercase letters denote beta-D-oxy-LNA units; lowercase letters denote DNA units; the subscript "s" denotes a phosphorothioate linkage; superscript Me denotes a DNA or beta-D-oxy-LNA unit containing a 5-methylcytosine base and C6 denotes a 6-aminohexyl-1-phosphate linkage.

After the solid phase synthesis, the GalNAc-cluster oligonucleotide conjugate is still bound on the solid support and still carries protection groups like the hydroxy protecting group $R^1$.

Cleavage from the support and deprotection can happen using methods known to the skilled in the art and described in the literature such as in Wincott et al.; Nucl. Acids Res. (1995) 23 (14): 2677-2684. Usually the GalNAc-cluster oligonucleotide conjugate is obtained in the form of a suitable salt such the ammonium salt or the alkali metal salt like the sodium or potassium salt.

The compounds disclosed herein have a nucleobase sequence selected from the group consisting of SEQ ID NO 1, 2, 3 and 4.

SEQ ID NO 1:
cagcgtaaagagagg

SEQ ID NO 2:
cacctatttaacatcagac

SEQ ID NO 3:
catcaactttcacttcag

SEQ ID NO 4:
aatgctacaaaaccca

EXAMPLES

Abbreviations

DIPEA diisopropylethyl amine
DMAP 4-(dimethylamino)-pyridine
ESI Electron Spry Ionization
EtOAc ethylacetate
EtOH ethanol
HRMS High-resolution mass spectrometry
HSQC-NMR Heteronuclear Single Quantum Coherence-Nuclear Magnetic Resonance
MeOH methanol
MS Molecular sieves
MsOH methanesulfonic acid
rt room temperature (20-25° C.)
SPOS solid phase oligonucleotide synthesis
T3P n-propylphosphonic acid anhydride
THF tetrahydrofuran
TBME methyl tert-butyl ether
Process Scheme:

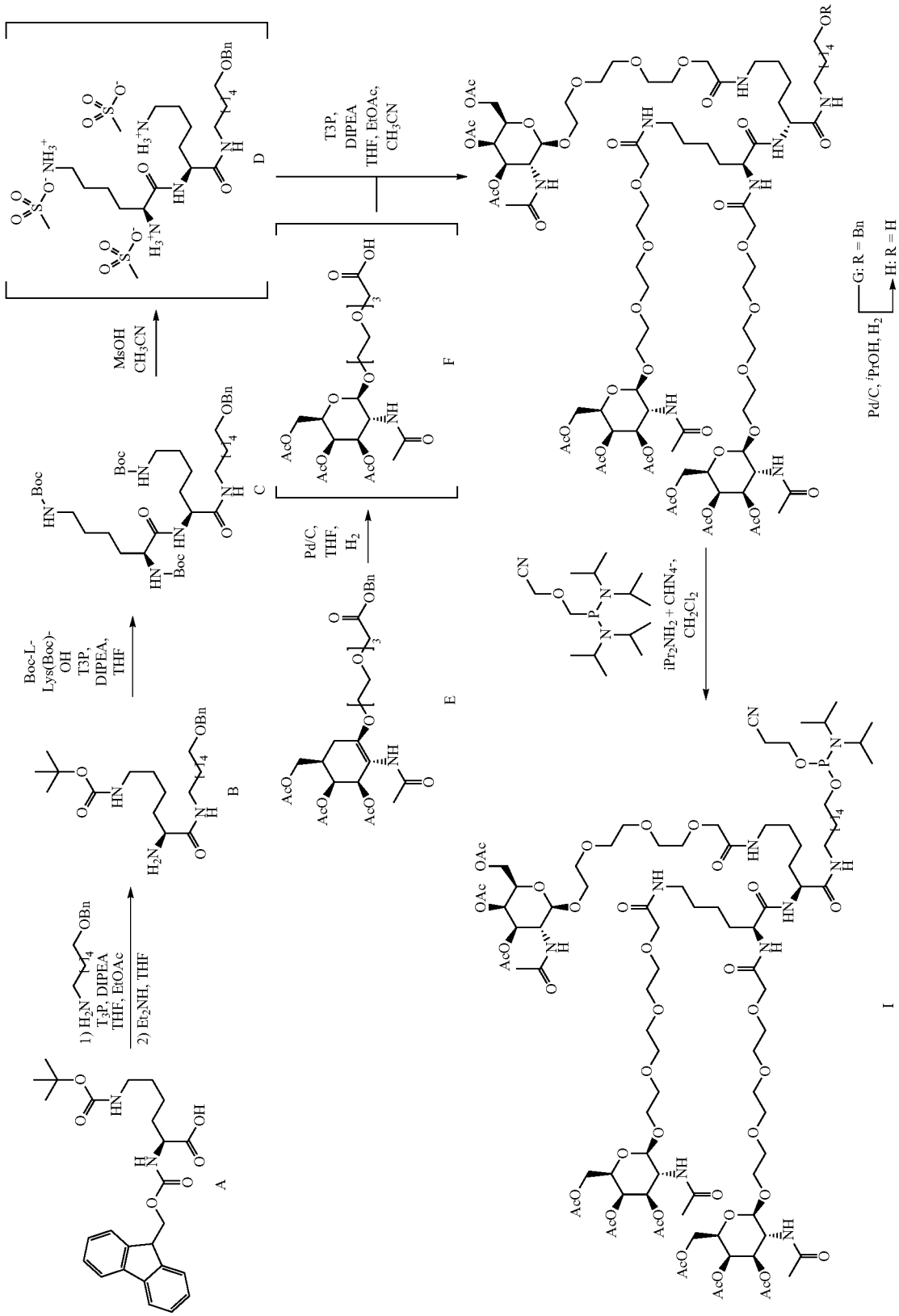

Example 1a (2S)-6-(tert-butoxycarbonylamino)-2-(9H-fluoren-9-ylmethoxycarbonylamino)hexanoic acid

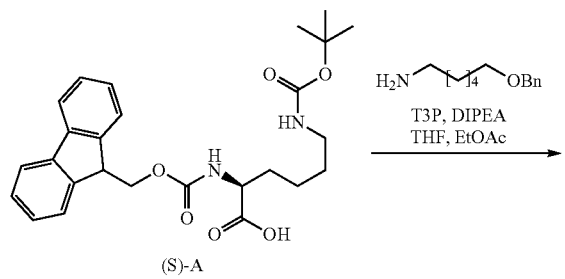

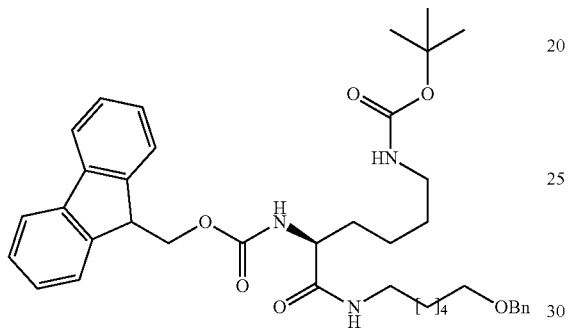

To a solution of Fmoc-L-Lys(Boc)-OH (54 g, 115 mmol), 6-benzyloxyhexyl-1-amine hydrochloride (prepared in accordance with WO2017084987A1) (29.5 g, 121 mmol) and N-ethyldiisopropylamine (78.4 ml, 461 mmol) in THF (540 ml) was added n-propylphosphonic acid anhydride (cyclic trimer 50% in EtOAc, 122 ml, 207 mmol,) over 30 s at 20-25° C. The resulting light yellow solution at pH 7-8 was stirred at 20-25° C. for 1 h. Water (540 ml), TBME (135 ml) and n-heptane (540 ml) were added sequentially to the reaction mixture and the biphasic mixture was extracted. The organic layer was concentrated and concentrated in vacuo to afford the target (S)-amide (79 g) which was used without further purification. HRMS (ESI): calc. for $C_{39}H_{51}N_3O_6$ (MH$^+$): 657.3778; found: 657.3781.

Example 1b (2R)-6-(tert-butoxycarbonylamino)-2-(9H-fluoren-9-ylmethoxycarbonylamino)hexanoic acid

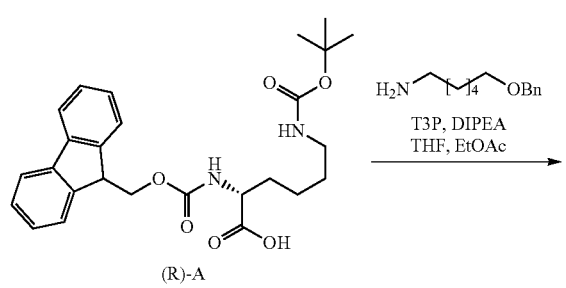

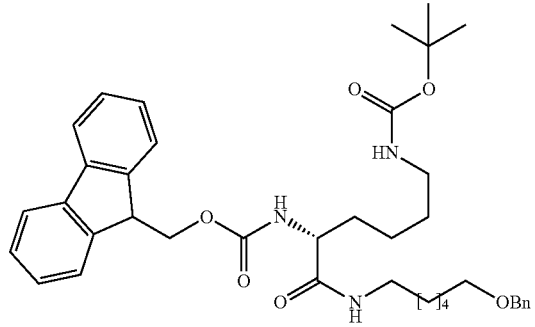

In the same fashion as for Example 1a, the crude (R)-amide was obtained as a white solid and used without further purification. HRMS (ESI): calc. for $C_{39}H_{51}N_3O_6$ (MH$^+$): 657.3778; found: 657.3789.

Example 2a tert-butyl N-[(5S)-5-amino-6-(6-benzyloxyhexylamino)-6-oxo-hexyl]carbamate

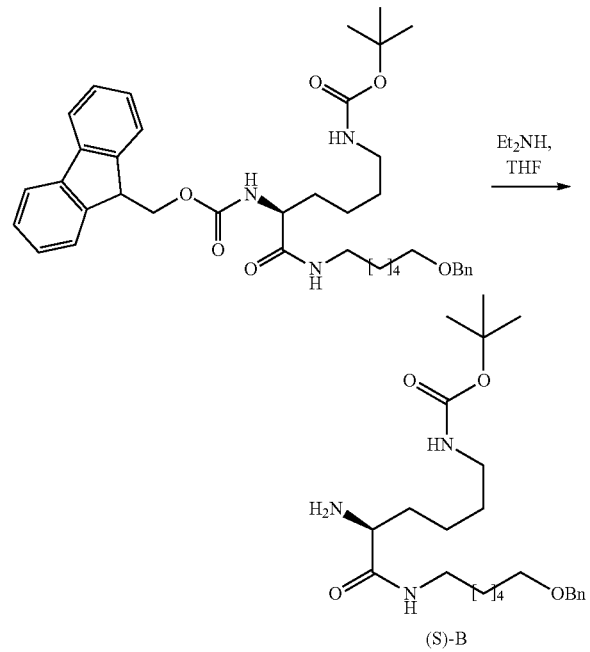

To a solution of the above crude amide (79 g, 120 mmol) in THF (237 ml) was added diethylamine (251 ml, 2.4 mol) and the colorless solution was stirred for 1.5 h at 20-25° C. Then the reaction mixture was concentrated and dried in vacuo to afford a light yellow oil, which was redissolved in TBME (521 ml) and water (521 ml). Methanesulfonic acid (7.02 ml, 108 mmol) was added to pH 4 and the layers were separated. The aqueous layer was reextracted with TBME (521 ml) and then basified with sodium hydroxide (32% in water, 12.9 ml, 139 mmol) to pH 14. The aqueous phase was extracted with TBME (521 ml), the organic layer was separated, dried over sodium sulfate, filtered, concentrated and dried in vacuo to afford (S)-B as a colorless oil (48.5 g, 97% yield over 2 steps). HRMS (ESI): calc. for $C_{24}H_{41}N_3O_6$ (MH$^+$): 435.3097; found: 435.3121.

Example 2b tert-butyl N-[(5R)-5-amino-6-(6-benzyloxyhexylamino)-6-oxo-hexyl]carbamate

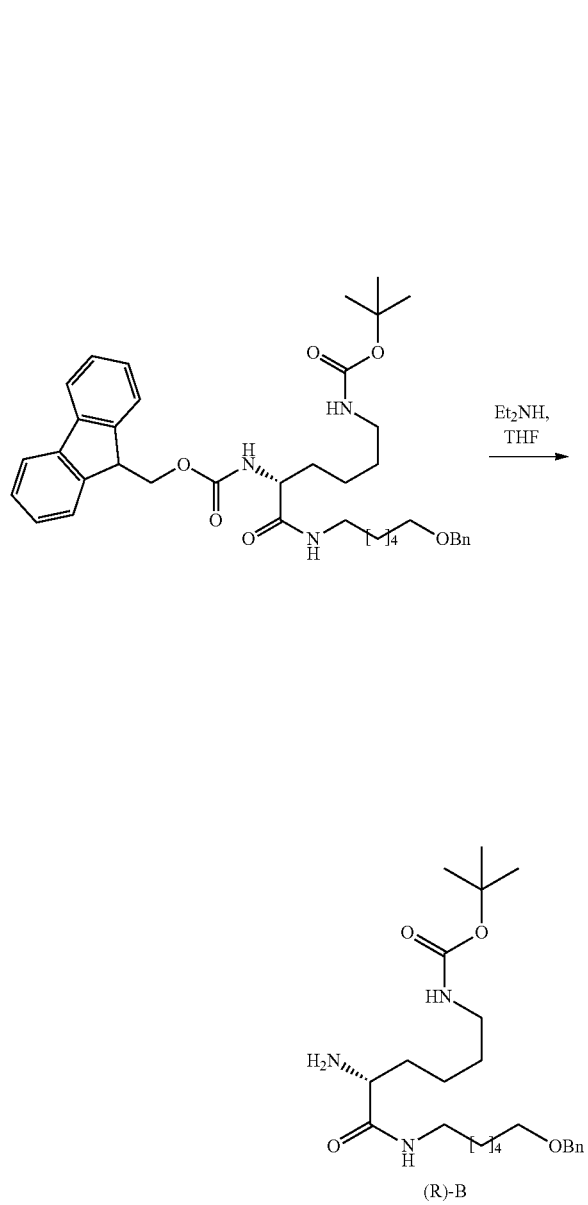

In the same fashion as for Example 2a, (R)-B was obtained as a light yellow oil (923 mg, 85% over two steps). HRMS (ESI): calc. for $C_{24}H_{41}N_3O_6$ (MH$^+$): 435.3097; found: 435.3113.

Example 3a tert-butyl N-[(5S)-6-(6-benzyloxyhexylamino)-6-oxo-5-[[(2S)-2,6-bis(tert-butoxycarbonylamino)hexanoyl]amino]hexyl]carbamate

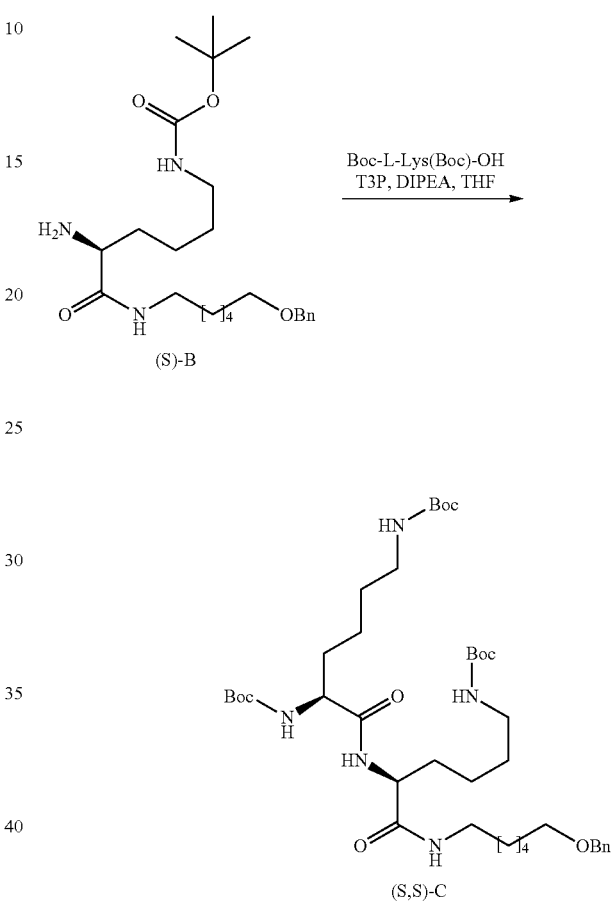

To a solution of (S)-B (48 g, 110 mmol), DIPEA (75 ml, 441 mmol) and Boc-L-Lys(Boc)-OH (45.8 g, 132 mmol) in THF (480 ml) was added T3P (50% in ethyl acetate, 97.4 ml, 165 mmol) over 30 s at 20-25° C. and the colorless solution was stirred for 45 min. Water (480 ml) was then added and the biphasic mixture was stirred for 5 min. n-heptane (480 ml) was added and the layers were separated. The organic layer was washed with 0.5M HCl in water (230 ml), 0.5M NaOH (230 ml), dried over sodium sulfate, filtered and concentrated. The crude product was dissolved in EtOH (45 ml) and n-heptane (428 ml) was added. The resulting white suspension was stirred for 16 h at 20-25° C. The suspension was filtered, the cake washed with EtOH/n-heptane (0.5/9.5, 50 ml) and the white solid dried in vacuo to afford (S,S)-C (63.3 g, 75% yield) as a white crystalline solid. HRMS (ESI): calc. for $C_{40}H_{69}N_5O_9$ (MH$^+$): 763.5095; found: 763.5098.

Example 3b tert-butyl N-[(5R)-6-(6-benzyloxyhexylamino)-6-oxo-5-[[(2S)-2,6-bis(tert-butoxycarbonylamino)hexanoyl]amino]hexyl]carbamate

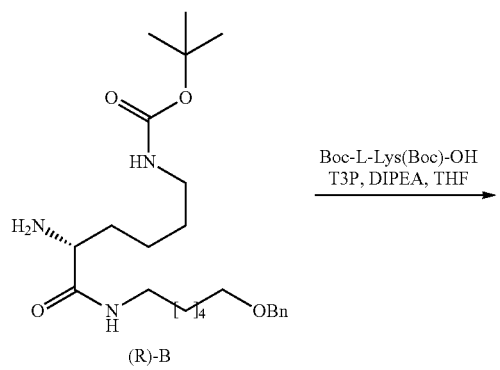

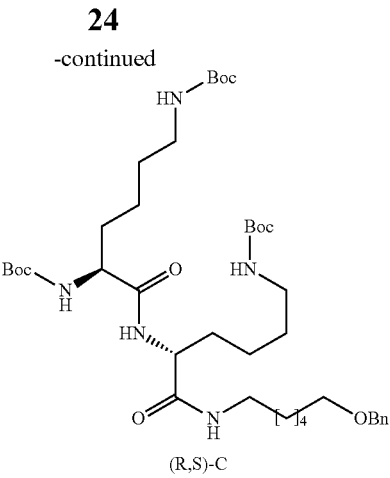

In the same fashion as for Example 3a, (R,S)-C was obtained as a white solid (16.4 g, 71%). HRMS (ESI): calc. for $C_{40}H_{69}N_5O_9$ (MH$^+$): 763.5095; found: 763.5076.

Example 4a (2S)-2,6-bis[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]-N-[(1S)-1-(6-benzyloxyhexylcarbamoyl)-5-[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]pentyl]hexanamide

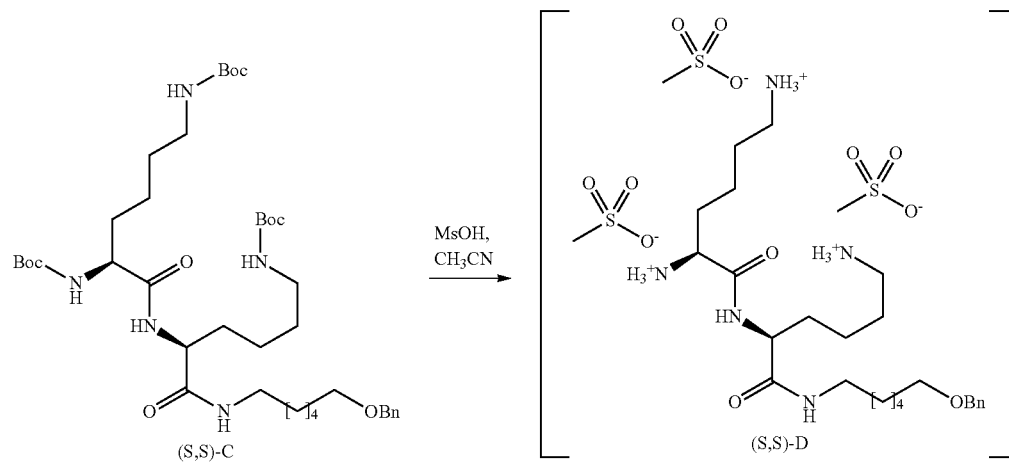

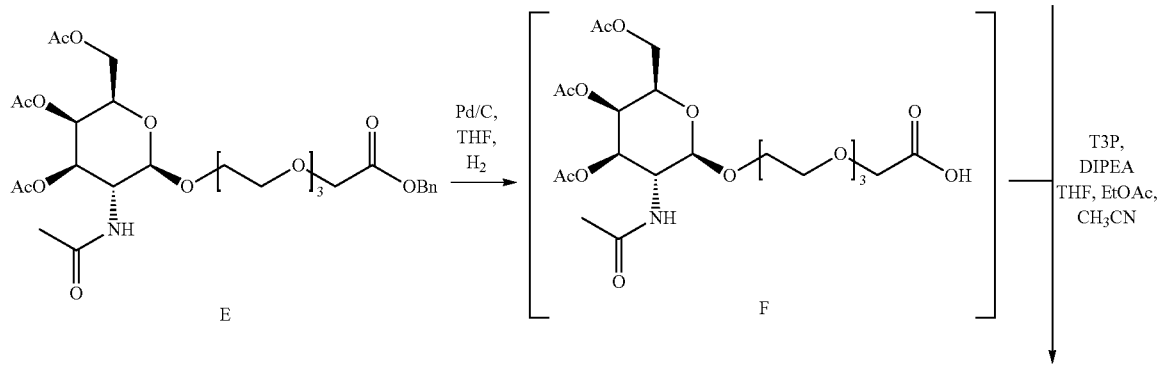

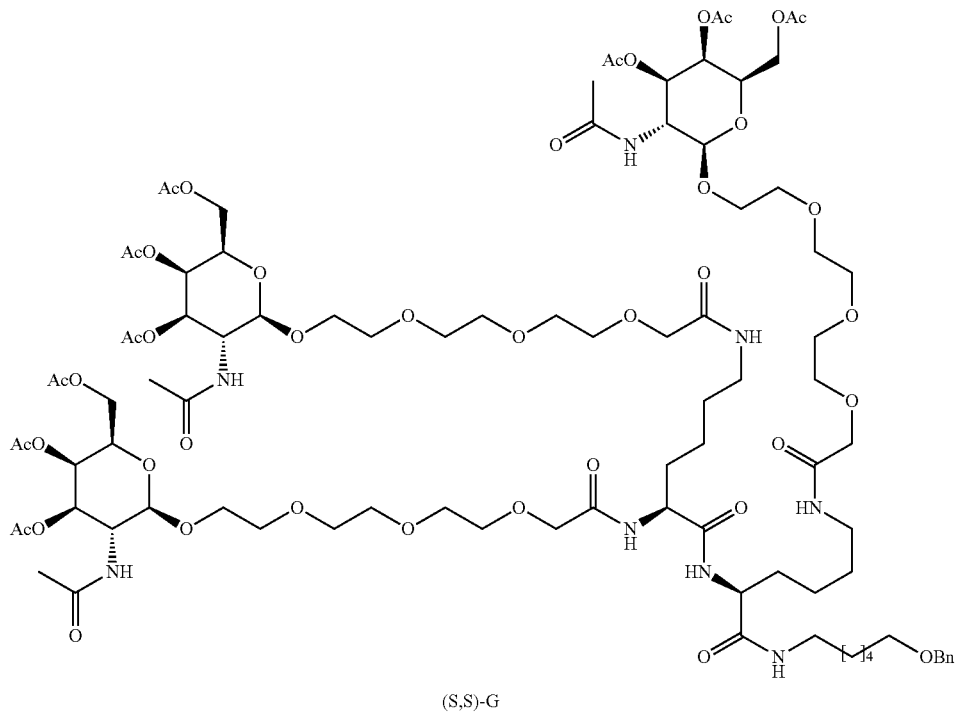

(S,S)-G (S,S)-C (36.1 g, 47.3 mmol) was suspended in acetonitrile (366 ml) and methanesulfonic acid (15.4 ml, 237 mmol) was added. The resulting yellowish, cloudy solution was heated to 55-60° C. After 20 min, additional acetonitrile (366 ml) was added to enable stirring. After 2h the oil bath was removed and the white slurry was used for the coupling. DIPEA (137 ml, 804 mmol) and a solution of F (which has been prepared in accordance with WO2017084987A (7.6% w/w, 1.35 kg, 191 mmol) were added to the above reaction mixture and the light yellow solution was warmed to 40-45° C. Then, T3P (50% in ethyl acetate, 139 ml, 237 mmol) was added over 5 min and the colorless solution was stirred at 40-45° C. After 30 min the reaction mixture was cooled to 20-25° C. and concentrated in vacuo to roughly 500 g. This crude solution was dissolved in 1M sodium bicarbonate (236 ml, 236 mmol) and was purified by reverse phase chromatography in 4 portions (Redisep $R_f$ C18, 360 g, $H_2O$/acetonitrile 100:0 to 70:30 to 60:40 to 10:90). The product-containing fractions were concentrated in vacuo to remove acetonitrile and then lyophilized to obtain a white foam which was azeotroped with acetonitrile (2×) to afford partly deacetylated (S,S)-G (77.1 g) as a white foam.

Reacetylation:

The above obtained (S,S)-G (77.1 g) were taken up in acetonitrile (231 ml) and treated with DMAP (465 mg, 3.81 mmol), DIPEA (4.86 ml, 28.6 mmol) and acetic anhydride (2.51 ml, 26.7 mmol) at 20-25° C. for 1 h. After dilution with water (1.01), the solution was purified again by reverse phase chromatography in 5 portions (Redisep $R_f$ C18, 360 g, $H_2O$/acetonitrile 100:0 to 70:30 to 65:35 to 0:100). The product-containing fractions were concentrated in vacuo to obtain a white foam which was azeotroped with acetonitrile to afford (S,S)-G (67.0 g, 87%) as a white foam. HRMS (ESI): calc. for $C_{91}H_{144}N_8O_{42}$ $((M+2H)/2^{2+})$: 1011.4762; found: 1011.4761.

Example 4b
(2S)-2,6-bis[[2-[2-[2-[2-[(2R,3R,4S,5R,6R)-3-acet-amido-6-ethyl-4,5-dimethyl-tetrahydropyran-2-yl]oxyethoxy]ethoxy]ethoxy]acetyl]amino]-N-[(1R)-1-(6-benzyloxyhexylcarbamoyl)-5-[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]pentyl]hexanamide
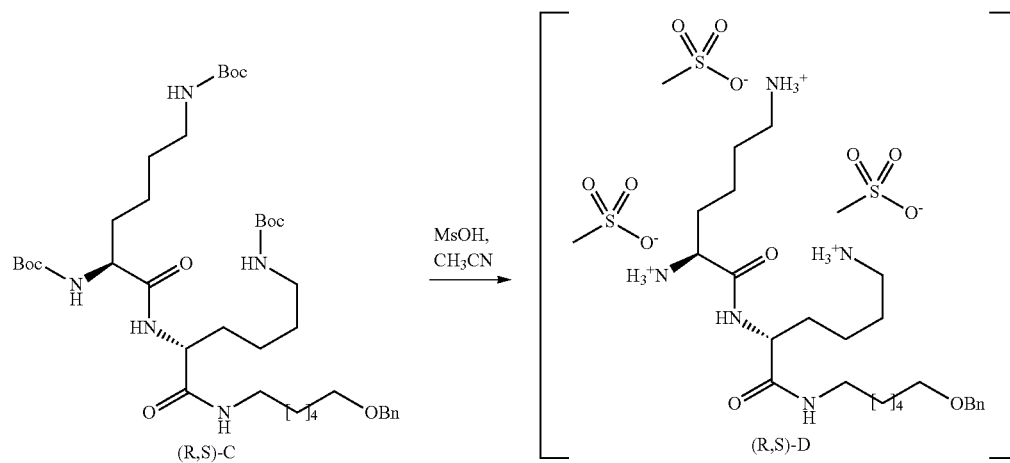
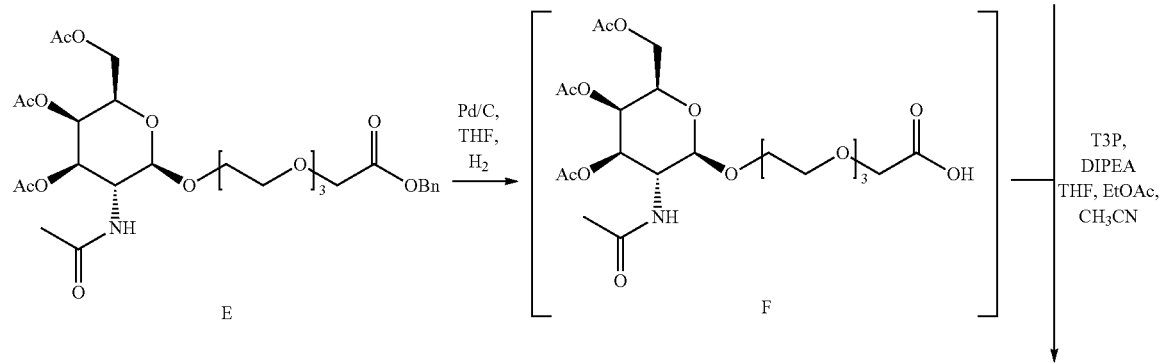

-continued
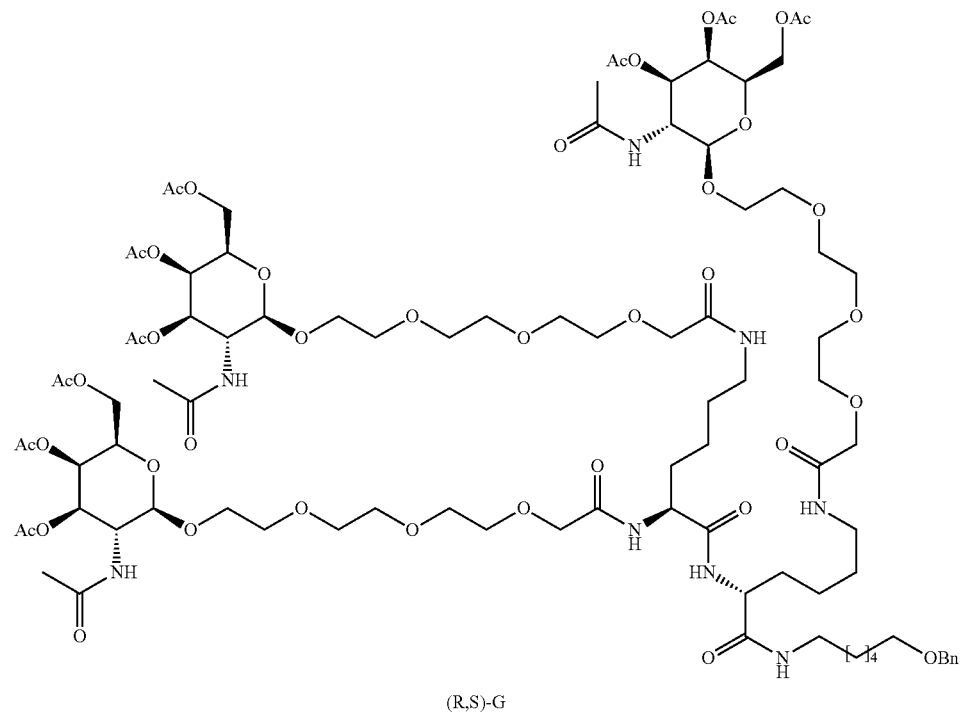
(R,S)-G
In the same fashion as for Example 4a but without the re-acetylation procedure, (R,S)-G was obtained as a white foam (29.1 g, 66%). HRMS (EI): calc. for $C_{91}H_{144}N_8O_{41}$ (M$^+$): 2020.9378; found: 2020.9365.

Example 5a (2S)-2,6-bis[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]-N-[(1S)-1-(6-hydroxyhexylcarbamoyl)-5-[[2-[2-[2-[2-[(2R,3R,4S,5R,6R)-3-acetamido-6-ethyl-4,5-dimethyl-tetrahydropyran-2-yl]oxyethoxy]-ethoxy]ethoxy]acetyl]amino]pentyl]hexanamide

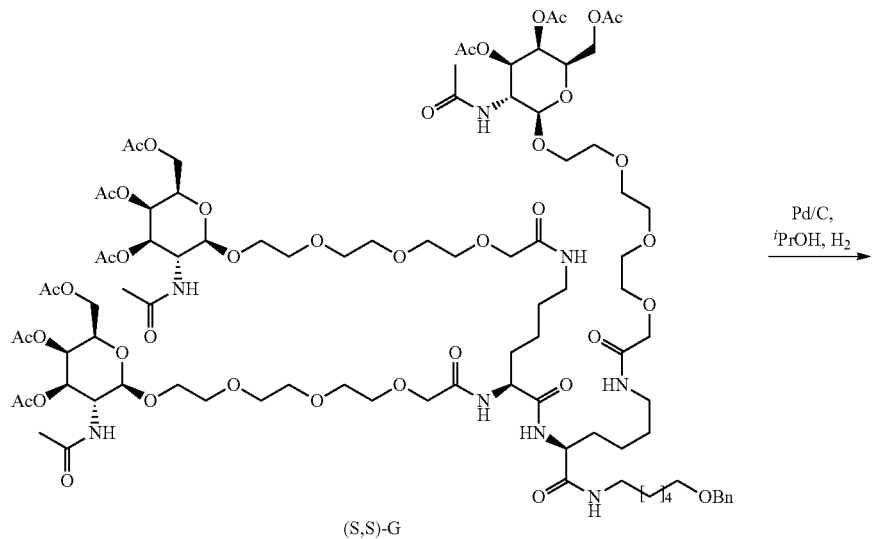

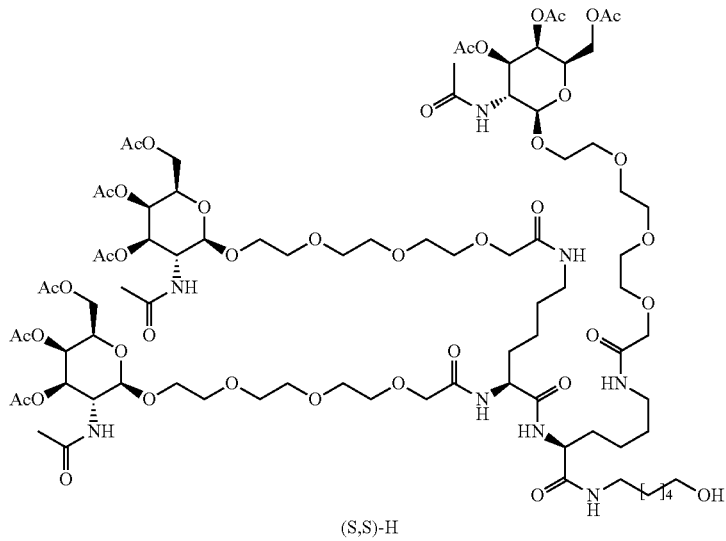

(S,S)-G (67.0 g, 33.1 mmol) was dissolved in 2-propanol (670 ml) and palladium on carbon 10% (3.8 g, 3.57 mmol) was added. The mixture was hydrogenated in a pressurized reactor at 20° C. under 60 bar of $H_2$ for 2 h. The suspension was filtered and the filter was washed with 2-propanol (150 ml). The resulting colorless solution was concentrated in vacuo and the residue azeotroped with acetonitrile (3×500 ml) to afford crude (S,S)-H (61.1 g, 95%) as a white foam which was used without further purification and stored at −20° C. HRMS (ESI): calc. for $C_{84}H_{139}N_8O_{42}$ (MH$^+$): 1930.8908; found: 1931.9004.

Example 5b (2S)-2,6-bis[[2-[2-[2-[2-[(2R,3R,4S,5R,6R)-3-acet-
amido-6-ethyl-4,5-dimethyl-tetrahydropyran-2-yl]
oxyethoxy]ethoxy]ethoxy]acetyl]amino]-N-[(1R)-1-
(6-hydroxyhexylcarbamoyl)-5-[[2-[2-[2-[2-[(2R,3R,
4S,5R,6R)-3-acetamido-6-ethyl-4,5-dimethyl-
tetrahydropyran-2-yl]oxyethoxy]-ethoxy]ethoxy]
acetyl]amino]pentyl]hexanamide

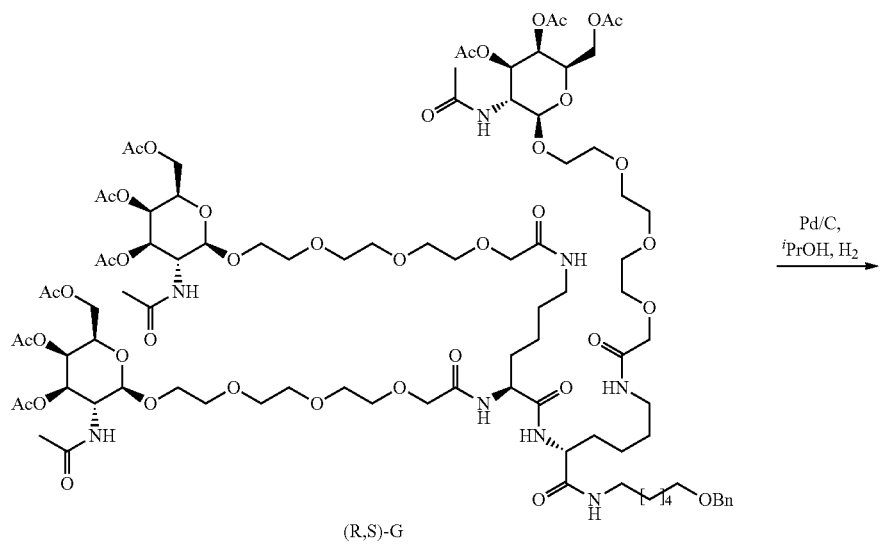

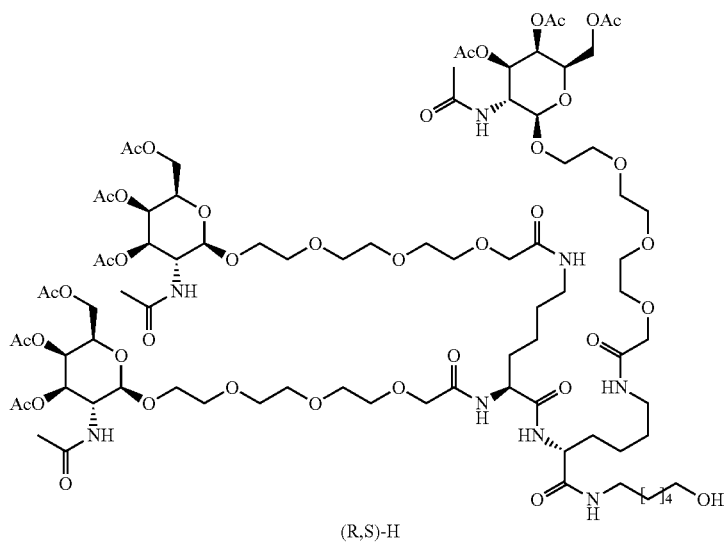

In the same fashion as for Example 5a, crude (R,S)-H was obtained as a white foam (29.1 g, quant.). LC-MS (ESI): calc. for $C_{84}H_{139}N_8O_{42}$ (MH$^+$): 1931.9; found: 1931.5.

Example 6a (2S)-2,6-bis[[2-[2-[2-[2-[rac-(2R,3R,4S,5R,6R)-3-acetamido-6-ethyl-4,5-dimethyl-tetrahydropyran-2-yl]oxyethoxy]ethoxy]ethoxy]acetyl]amino]-N-[(1S)-1-[6-[2-cyanoethoxy-(diisopropylamino)phosphanyl]oxyhexylcarbamoyl]-5-[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]pentyl]hexanamide

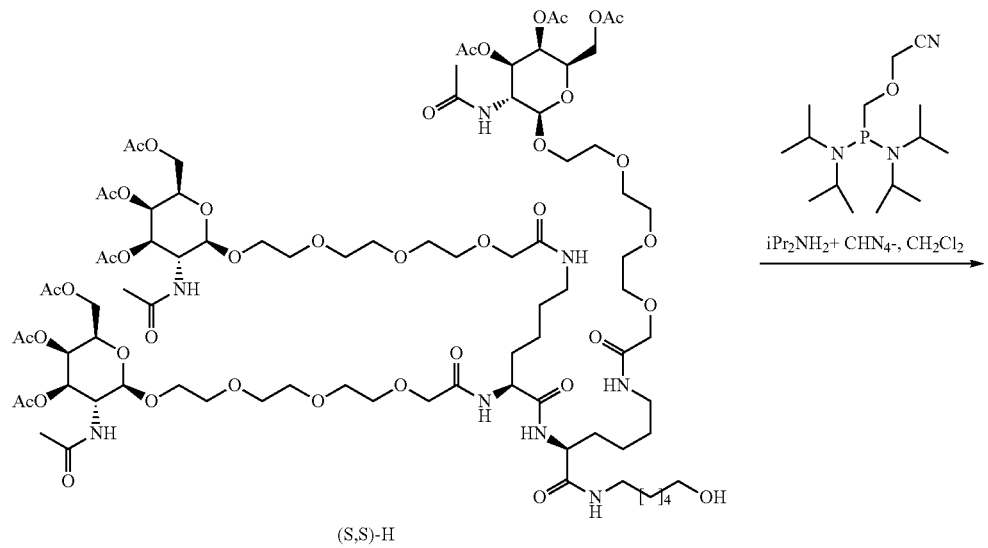

To a solution of (S,S)-H (3.4 g, 1.76 mmol) in anhydrous dichloromethane (20 ml) was added 3-((bis(diisopropylamino)phosphino)oxy)propanenitrile (902 mg, 2.99 mmol,) and Diisopropyl-ammonium tetrazolide (151 mg, 0.88 mmol). The light yellow solution was stirred at 20-25° C. for 1 h. The reaction mixture was diluted with TBME and purified directly by preparative chromatography (Redisep R$_f$ Gold Cyano, 275 g, TBME (containing 1% v/v NEt$_3$)/acetonitrile 90:10 to 70:30). The product containing fractions were concentrated in vacuo to afford (S,S)-I (3.0 g, 80%) as a white foam. $^{31}$P NMR (162 MHz, DMSO-d6): ppm 146.32; HRMS (Nanospray from anhydrous CHCl$_3$): calc. for C$_{91}$H$_{144}$N$_8$O$_{42}$ ((M+2H)/2$^{2+}$): 1066.5066; found: 1066.5078.

Example 6b
(2S)-2,6-bis[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]-N-[(1R)-1-[6-[2-cyanoethoxy-(diisopropylamino)phosphanyl]oxyhexylcarbamoyl]-5-[[2-[2-[2-[2-[(2R,3R,4S,5R,6R)-3-acetamido-6-ethyl-4,5-dimethyl-tetrahydropyran-2-yl]oxyethoxy]ethoxy]ethoxy]acetyl]amino]pentyl]hexanamide
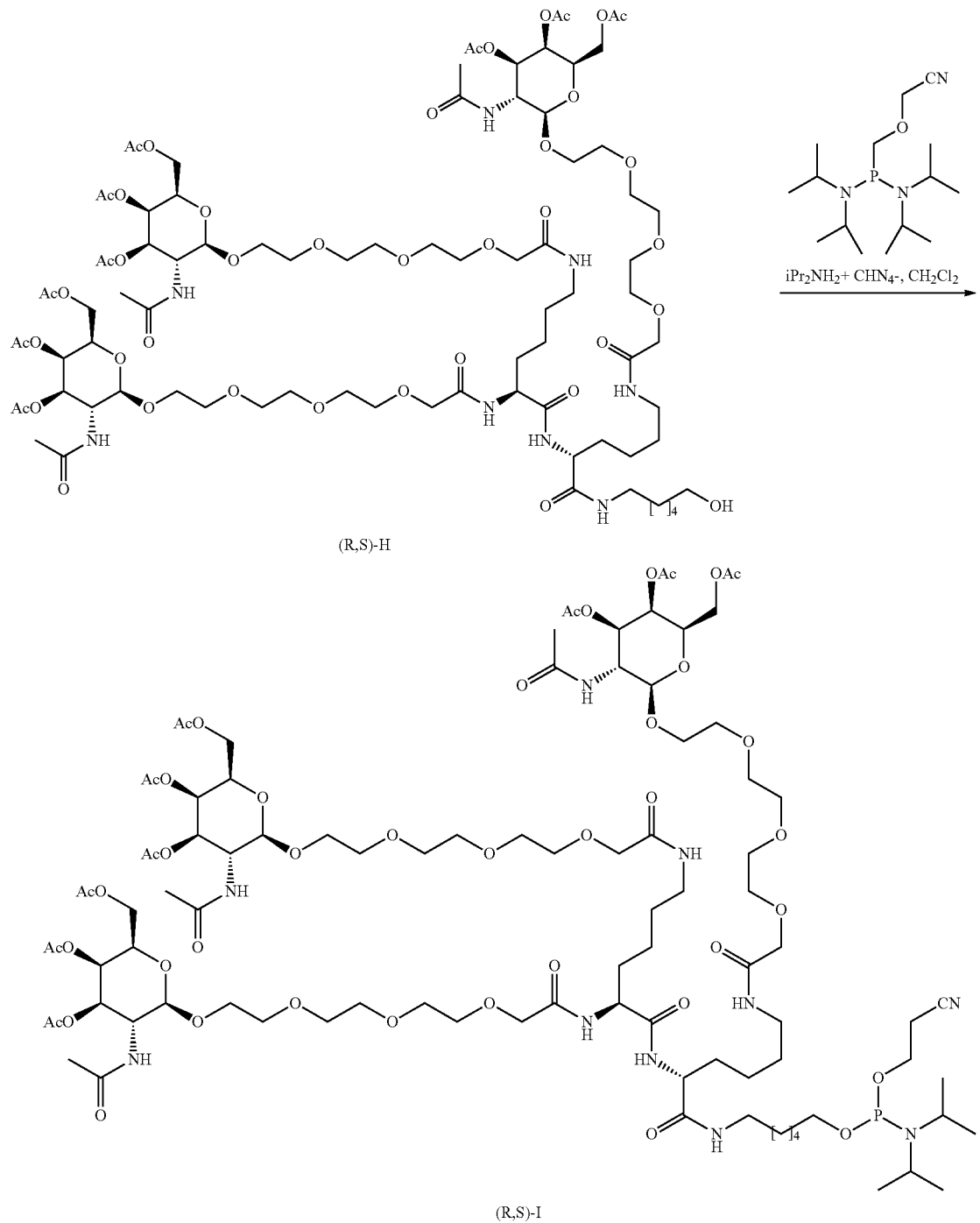

To a solution of (R,S)-H (2.5 g, 1.29 mmol) in acetonitrile (20 ml, dried over $CaH_2$) was added 3-((bis(diisopropylamino)phosphino)oxy)propanenitrile (624 mg, 2.07 mmol,) and Diisopropyl-ammonium tetrazolide (44.3 mg, 0.26 mmol). The colorless solution was stirred at 20-25° C. for 1.5 h. The reaction mixture concentrated in vacuo to a volume of 12 ml and was applied preparative chromatography (Redisep $R_f$ Gold Cyano, 275 g, TBME/acetonitrile 95:5 to 75:25). The product containing fractions were concentrated in vacuo to afford (R,S)-I (2.1 g, 76%) as a colorless wax. $^{31}P$ NMR (162 MHz, DMSO-d6): ppm 146.83.

For the solid phase oligonucleotide synthesis (SPOS), either (S,S)-I and (R,S)-I was dissolved in anhydrous MeCN or $CH_2Cl_2$ to afford a 0.1-0.2M solution. This solution was dried for one hour over 4 Å MS, 3 Å MS, anhydrous $K_2CO_3$, basic activated alumina, $CaCl_2$ or $CaH_2$ and then used directly on an oligonucleotide synthesizer.

Solid-Phase Oligonucleotide Synthesis

GalNAc-cluster-modified LNA/DNA was produced by standard phosphoramidite chemistry (see WO2017084987A1 and WO2018215391A1) on solid phase at a scale of 1 or 20 μmol on a BioAutomation Mermade 12 or at a 0.2, 0.95 or 1.9 mmol scale using an AKTA Oligopilot 100 (GE Healthcare, Freiburg, Germany). Solid supports used include Primer Support 5G Unylinker 200 (GE Healthcare, Freiburg, Germany), Primer Support 5G Unylinker 350 (GE Healthcare, Freiburg, Germany) or Kinovate Nitto-Phase HL Unylinker 400. Oligonucleotides containing, 2-OCH$_2$-4 bridged nucleotides (Sigma-Aldrich, SAFC, Hamburg, Germany) and DNA (Sigma-Aldrich, SAFC, Hamburg, Germany) were generated employing the corresponding phosphoramidites. The above prepared solutions of GalNAc-cluster phosphoramidite (S,S)-I and (R,S)-I in MeCN or $CH_2Cl_2$ were used with standard SPOS activators, such as 4,5-dicyanoimidazole (with and without N-methylimidazole) or tetrazole activators such as 5-(benzylthio)-1H-tetrazole or Activator 42, employing 1.5-4.0 equivalents of phosphoramidite, an amidite to activator ratio of 30/70-40/60 and coupling times of 10-30 min. Oxidation is performed by organic oxidants such as camphorsulfonyloxaziridine, cumene hydroperoxide, tert-butylhydrogenperoxide or iodine in pyridine/$H_2O$ (9:1). Thiolation can be effected by standard thiolation reagents used for SPOS, such as 3-amino-1,2,3-dithiazole-5-thione (xhanthane hydride), 3-dimethylamino-1,2,3-dithiazole-5-thione, 3-ethoxy-1,2,4-dithiazoline-5-one, Beaucage reagent or phenylacetic acid disulfide in their respective solvents. No capping step was employed for the coupling of GalNAc-cluster phosphoramidites. Cleavage and deprotection was achieved by methods known in the field (Wincott F. et al. Nucleic Acid Research, 1995, 23,14, 2677-84), such as concentrated $NH_4OH$ (28-33%) at temperatures between 25-55° C. The deprotected and dried crude GalNAc-clusters modified LNA as ammonium salt were characterized and the identity was confirmed with ion pair HPLC-MS.

They can be purified by standard purification methods for oligonucleotides (see e.g. WO2018215391A1).

(Uppercase letters denote beta-D-oxy-LNA units; lowercase letters denote DNA units; the subscript "s" denotes a phosphorothioate linkage; superscript Me denotes a DNA or beta-D-oxy-LNA unit containing a 5-methylcytosine base and AM-C6 denote a 6-aminohexyl-1-phosphate linkage).

Example 7a

Synthesis of 5'-(S,S)-GalNAc-C6-caG$_s$$^{Me}$C$_s$-G$_s$t$_s$a$_s$a$_s$g$_s$a$_s$g$_s$a$_s$G$_s$G-3'

According to the above standard SPOS conditions using (S,S)-I, the title product was synthesized on a 1.9 mmol scale on an AKTA Oligopilot 100 (GE Healthcare, Freiburg, Germany). The deprotected and concentrated crude oligonucleotide as ammonium salt was purified by reverse-phase HPLC and, after ultrafiltration/diafiltration and lyophilization, afforded the sodium salt of 5'-(S,S)-GalNAc-C6-caG$_s$$^{Me}$C$_s$G$_s$t$_s$a$_s$a$_s$a$_s$g$_s$a$_s$g$_s$a$_s$G$_s$G-3' (1.7 g, 87.0 a % HPLC purity) as a white lyophilisate. IP-RP-HPLC-HRMS (ESI): calc. for $C_{220}H_{303}N_{76}O_{111}P_{15}S_{12}$ (M$^-$): 6633.3115; found: 6633.3089. The epimeric purity was determined by $^1$H-$^{13}$C-HSQC-NMR to be >95% (LOD). Additionally, hydrolysis in 6M HCl, derivatization of the free amino acids and gas chromatographic separation of the lysine enantiomers on CHIRASIL VAL showed an epimeric purity of 99.8%.

Example 7b

Synthesis of 5'-(R,S)-GalNAc-C6-caG$_s$$^{Me}$C$_s$-G$_s$t$_s$a$_s$a$_s$a$_s$g$_s$a$_s$g$_s$a$_s$G$_s$G-3'

According to the above standard SPOS conditions using (R,S)-I, the title product was synthesized on a 1.9 mmol scale on an AKTA Oligopilot 100 (GE Healthcare, Freiburg, Germany). The deprotected and concentrated crude oligonucleotide as ammonium salt was purified by reverse-phase HPLC and, after ultrafiltration/diafiltration and lyophilization, afforded the sodium salt of 5'-(R,S)-GalNAc-C6-caG$_s$$^{Me}$C$_s$G$_s$t$_s$a$_s$a$_s$a$_s$g$_s$a$_s$g$_s$a$_s$G$_s$G-3' (1.6 g, 91.6 a % HPLC purity) as a white lyophilisate. IP-RP-HPLC-HRMS (ESI): calc. for $C_{220}H_{303}N_{76}O_{111}P_{15}S_{12}$ (M$^-$): 6633.3115; found: 6633.3134. The epimeric purity was determined by $^1$H-$^{13}$C-HSQC-NMR to be >95% (LOD). Additionally, hydrolysis in 6M HCl, derivatization of the free amino acids and gas chromatographic separation of the lysine enantiomers on CHIRASIL VAL showed an epimeric purity of <95.6%.

Example 8a

Synthesis of 5'-(S,S)-GalNAc-C6-ca$^{Me}$C$_s$$^{Me}$C$_s$t$_s$a$_s$-t$_s$t$_s$t$_s$a$_s$a$_s$c$_s$a$_s$t$_s$c$_s$A$_s$ G$_s$A$_s$$^{Me}$C-3'

According to the above standard SPOS conditions using (S,S)-I, the title product was synthesized on a 0.2 mmol scale on an AKTA Oligopilot 100 (GE Healthcare, Freiburg, Germany). The deprotected and concentrated crude oligonucleotide as ammonium salt was purified by IEX-MPLC and, after ultrafiltration/diafiltration and lyophilization, afforded the sodium salt of 5'-(S,S)-GalNAc-C6-ca$^{Me}$C$_s$-$^{Me}$C$_s$t$_s$a$_s$t$_s$t$_s$a$_s$a$_s$c$_s$a$_s$t$_s$c$_s$A$_s$G$_s$A$_s$$^{Me}$C-3' (350 mg, 79.1 a % HPLC purity) as a white lyophilisate. IP-RP-HPLC-HRMS (ESI): calc. for $C_{259}H_{359}N_{76}O_{135}P19S16$ (M$^-$): 7793.4109; found: 7793.4127. The epimeric purity was determined by $^1$H-$^{13}$C-HSQC-NMR to be >96% (LOD). Additionally, hydrolysis in 6M HCl, derivatization of the free amino acids and gas chromatographic separation of the lysine enantiomers on CHIRASIL VAL showed an epimeric purity of 99.8%.

Example 8b

Synthesis of 5'-(R,S)-GalNAc-C6-ca$^{Me}$C$_s$$^{Me}$C$_s$t$_s$a$_s$-t$_s$t$_s$t$_s$a$_s$a$_s$c$_s$a$_s$t$_s$c$_s$A$_s$G$_s$ A$_s$$^{Me}$C-3'

According to the above standard SPOS conditions using (R,S)-I, the title product was synthesized was produced on a 0.2 mmol scale on an AKTA Oligopilot 100 (GE Healthcare, Freiburg, Germany). The deprotected and concentrated crude oligonucleotide as ammonium salt was purified by IEX-MPLC and, after ultrafiltration/diafiltration and lyophilization, afforded the sodium salt of 5'-(R,S)-GalNAc-C6-ca$^{Me}$C$_s$$^{Me}$C$_s$t$_s$a$_s$t$_s$t$_s$a$_s$a$_s$c$_s$a$_s$t$_s$c$_s$A$_s$G$_s$A$_s$$^{Me}$C-3' (630 mg, 82.9 a % HPLC) as a white lyophilisate. IP-RP-HPLC-HRMS (ESI): calc. for $C_{259}H_{359}N_{76}O_{135}P_{19}S_{16}$ (M$^-$): 7793.4109; found: 7793.4127. The epimeric purity was determined by $^1$H-$^{13}$C-HSQC-NMR to be >96% (LOD). Additionally, hydrolysis in 6M HCl, derivatization of the free amino acids and gas chromatographic separation of the lysine enantiomers on CHIRASIL VAL showed an epimeric purity of >95.4%.

Example 9a

Synthesis of 5'-(S,S)-GalNAc-C6-caT$_s$$^{Me}$C$_s$A$_s$a$_s$c-$_s$t$_s$t$_s$t$_s$c$_s$a$_s$c$_s$t$_s$t$_s$$^{Me}$C$_s$A$_s$G$_s$-3'

According to the above standard SPOS conditions using (S,S)-I, the title product was synthesized on 2*1.9 mmol scale on an AKTA Oligopilot 100 (GE Healthcare, Freiburg, Germany). The deprotected and concentrated crude oligonucleotide as ammonium salt was purified by IEX-MPLC, followed by reverse-phase HPLC and, after ultrafiltration/diafiltration and lyophilization, afforded the sodium salt of 5'-(S,S)-GalNAc-C6-caT$_s$$^{Me}$C$_s$A$_s$a$_s$c$_s$t$_s$t$_s$t$_s$c$_s$a$_s$c$_s$t$_s$t$_s$$^{Me}$C$_s$-A$_s$G$_s$-3' (12.5 g, 92.7 a % HPLC purity) as a white lyophilisate. IP-RP-HPLC-HRMS (ESI): calc. for $C_{248}H_{346}N_{68}O_{133}P_{18}S_{15}$ (M$^-$): 7441.3490; found: 7441.3730. The epimeric purity was determined by $^1$H-$^{13}$C-HSQC-NMR to be >98% (LOD). Additionally, hydrolysis in 6M HCl, derivatization of the free amino acids and gas chromatographic separation of the lysine enantiomers on CHIRASIL VAL showed an epimeric purity of 99.6%.

Example 9b

Synthesis of 5'-(R, S)-GalNAc-C6-caT$_s$$^{Me}$C$_s$A$_s$a$_s$c-$_s$t$_s$t$_s$t$_s$c$_s$a$_s$c$_s$t$_s$t$_s$$^{Me}$C$_s$A$_s$G$_s$-3'

According to the above standard SPOS conditions using (R,S)-I, the title product was synthesized was produced on a 1.9 mmol scale on an AKTA Oligopilot 100 (GE Healthcare, Freiburg, Germany). The deprotected and concentrated crude oligonucleotide as ammonium salt was purified by reverse-phase HPLC and, after ultrafiltration/diafiltration and lyophilization, afforded the sodium salt of 5'-(R,S)-GalNAc-C6-caT$_s$$^{Me}$C$_s$A$_s$a$_s$c$_s$t$_s$t$_s$t$_s$c$_s$a$_s$c$_s$t$_s$t$_s$$^{Me}$C$_s$A$_s$G$_s$-3' (6.0 g, 82.0 a % HPLC) as a white lyophilisate. IP-RP-HPLC-HRMS (ESI): calc. for $C_{248}H_{346}N_{68}O_{133}P_{18}S_{15}$ (M$^-$): 7441.3490; found: 7441.3508. The epimeric purity was determined by $^1$H$^{13}$C-HSQC-NMR to be >98% (LOD). Additionally, hydrolysis in 6M HCl, derivatization of the free amino acids and gas chromatographic separation of the lysine enantiomers on CHIRASIL VAL showed an epimeric purity of >97.0%.

Example 10a

Synthesis of 5'-(S,S)-GalNAc-C6$_s$-A$_s$A$_s$T$_s$g$_s$c$_s$t-$_s$a$_s$c$_s$a$_s$a$_s$a$_s$c$_s$$^{Me}$C$_s$$^{Me}$C$_s$A-3'

According to the above standard SPOS conditions using (S,S)-I, the title product was synthesized on 0.95 mmol scale on an AKTA Oligopilot 100 (GE Healthcare, Freiburg, Germany). The deprotected and concentrated crude oligonucleotide as ammonium salt was purified by reverse-phase HPLC and, after ultrafiltration/diafiltration and lyophilization, afforded the sodium salt of 5'-(S,S)-GalNAc-C6$_s$-A$_s$A$_s$T$_s$g$_s$c$_s$t$_s$a$_s$c$_s$a$_s$a$_s$a$_s$c$_s$$^{Me}$C$_s$$^{Me}$C$_s$A-3' (1.6 g, 87.7 a % HPLC purity) as a white lyophilisate. IP-RP-HPLC-HRMS (ESI): calc. for $C_{229}H_{318}N_{72}O_{113}P_{16}S_{16}$ (M$^-$): 6891.2684; found: 6891.2714. The epimeric purity was determined by $^1$H-$^{13}$C-HSQC-NMR to be >94% (LOD). Additionally, hydrolysis in 6M HCl, derivatization of the free amino acids and gas chromatographic separation of the lysine enantiomers on CHIRASIL VAL showed an epimeric purity of 99.6%.

Example 10b

Synthesis of 5'-(R,S)-GalNAc-C6$_s$-A$_s$A$_s$T$_s$g$_s$c$_s$t-$_s$a$_s$c$_s$a$_s$a$_s$a$_s$c$_s$$^{Me}$C$_s$$^{Me}$C$_s$A-3'

According to the above standard SPOS conditions using (R,S)-I, the title product was synthesized was produced on a 0.95 mmol scale on an AKTA Oligopilot 100 (GE Healthcare, Freiburg, Germany). The deprotected and concentrated crude oligonucleotide as ammonium salt was purified by reverse-phase HPLC and, after ultrafiltration/diafiltration and lyophilization, afforded the sodium salt of 5'-(R,S)-GalNAc-Ch$_s$-A$_s$A$_s$T$_s$g$_s$c$_s$t$_s$a$_s$c$_s$a$_s$a$_s$a$_s$c$_s$$^{Me}$C$_s$$^{Me}$C$_s$A-3' (2.0 g, 88.0 a % HPLC) as a white lyophilisate. IP-RP-HPLC-HRMS (ESI): calc. for $C_{229}H_{318}N_{72}O_{113}P_{16}S_{16}$ (M$^-$): 6891.2684; found: 6891.2715. The epimeric purity was determined by $^1$H-$^{13}$C-HSQC-NMR to be >95% (LOD). Additionally, hydrolysis in 6M HCl, derivatization of the free amino acids and gas chromatographic separation of the lysine enantiomers on CHIRASIL VAL showed an epimeric purity of 99.4%.

The invention claimed is:

1. A process for the preparation of epimerically pure GalNAc phosphoramidite epimers of formula I,

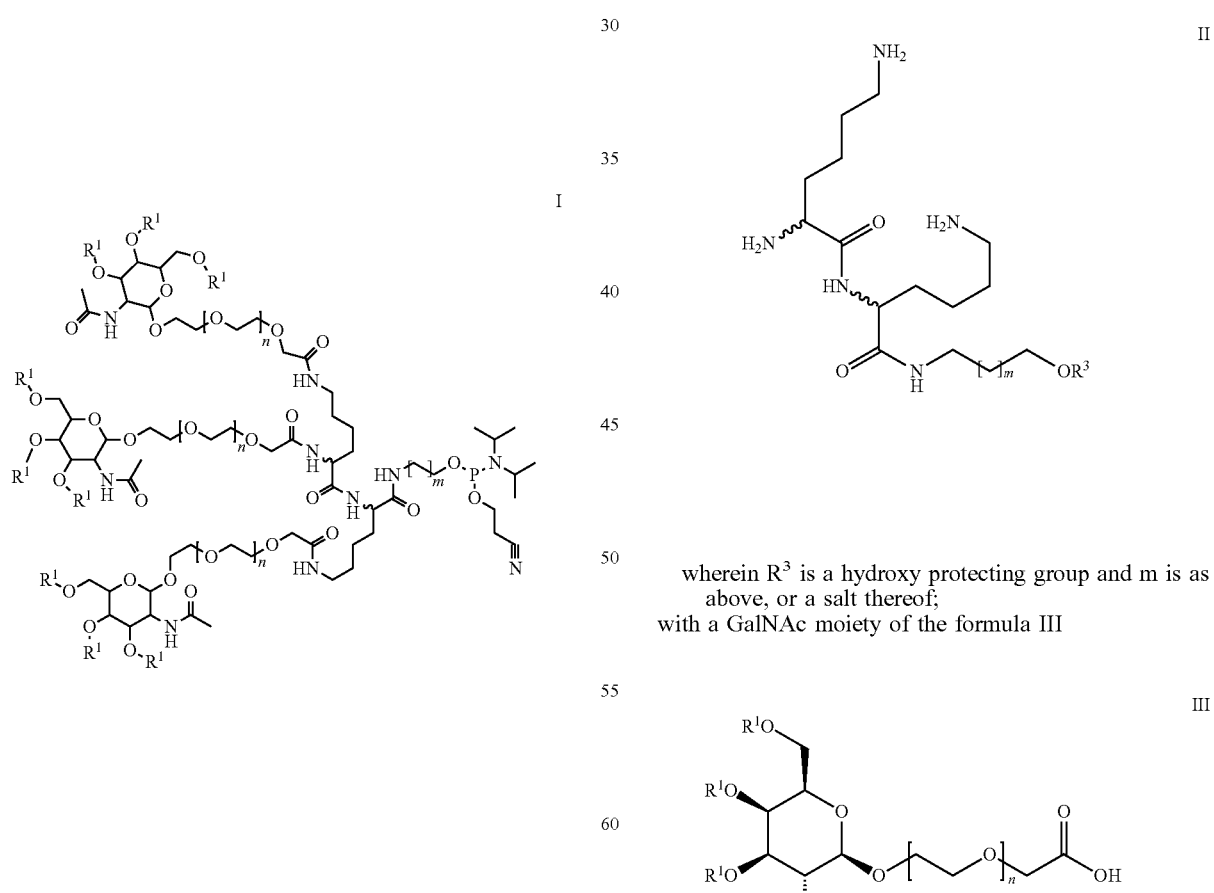

wherein $R^1$ is a hydroxy protecting group, n is an integer from 0 to 10, and m is an integer from 0 to 20, and corresponding enantiomers and/or optical isomers thereof, the process comprising the steps of:

a) coupling a compound of formula II, wherein $R^3$ is a hydroxy protecting group and m is as above, or a salt thereof;
with a GalNAc moiety of the formula III wherein R¹ and n is as above to form the GalNAc amide of formula IV

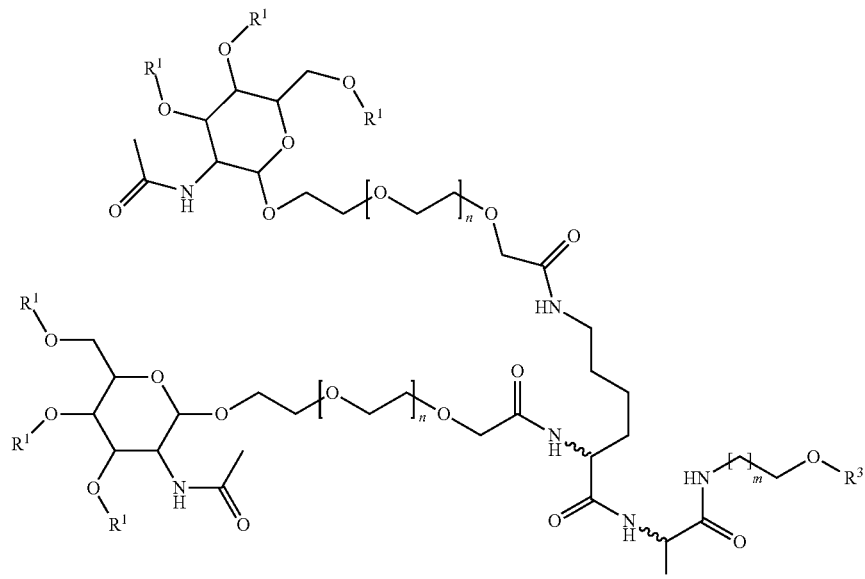

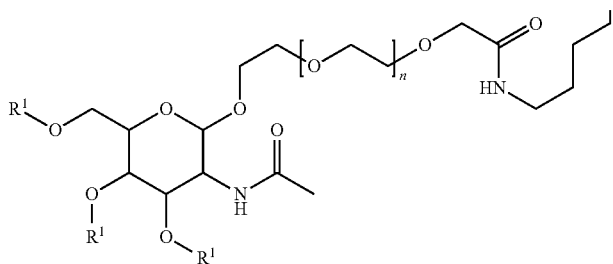

wherein R¹, R³, n and m are as above;
b) removing the hydroxyl protecting group R³ to form the free alcohol of the GalNAc amide of formula IV; and
c) reacting the free alcohol of the GalNAc amide of formula IV with a phosphoroamidating agent to form the GalNAc phosphoramidite epimer of the formula I.

2. The process of claim 1, wherein R¹ is an acyl group.
3. The process of claim 2, wherein R¹ is a $C_{1-6}$-alkylcarbonyl group which is optionally substituted by $C_{1-6}$-alkyl or phenyl.
4. The process of claim 1, wherein n is an integer from 0 to 5 and m is an integer from 0 to 10.
5. The process of claim 4, wherein R¹ is acetyl, n is 2 and m is 5.
6. The process of claim 1, wherein R³ is benzyl.
7. The process of claim 1, wherein the formula I comprises GalNAc phosphoramidite epimers of the formulas Ib to Ie.

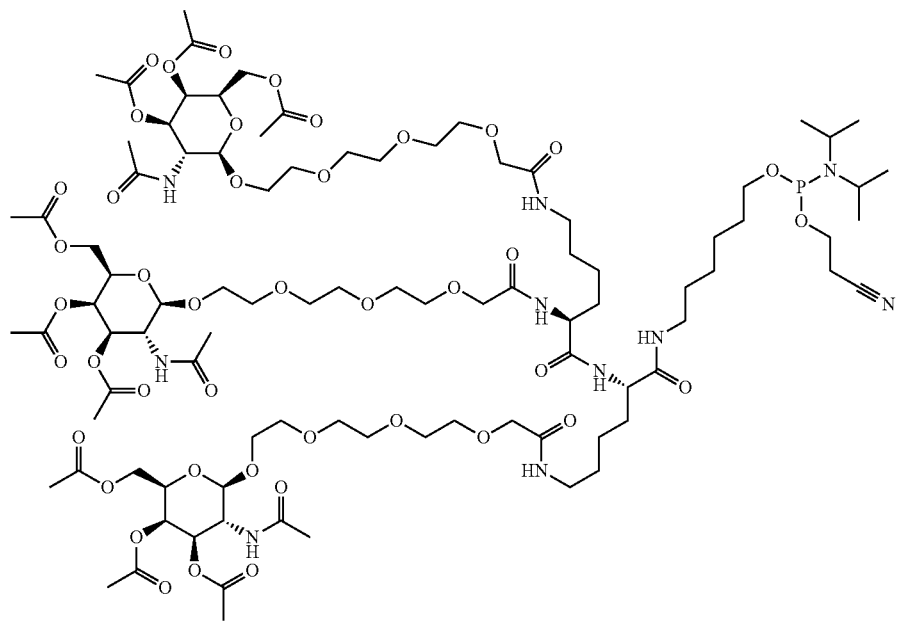
Ib
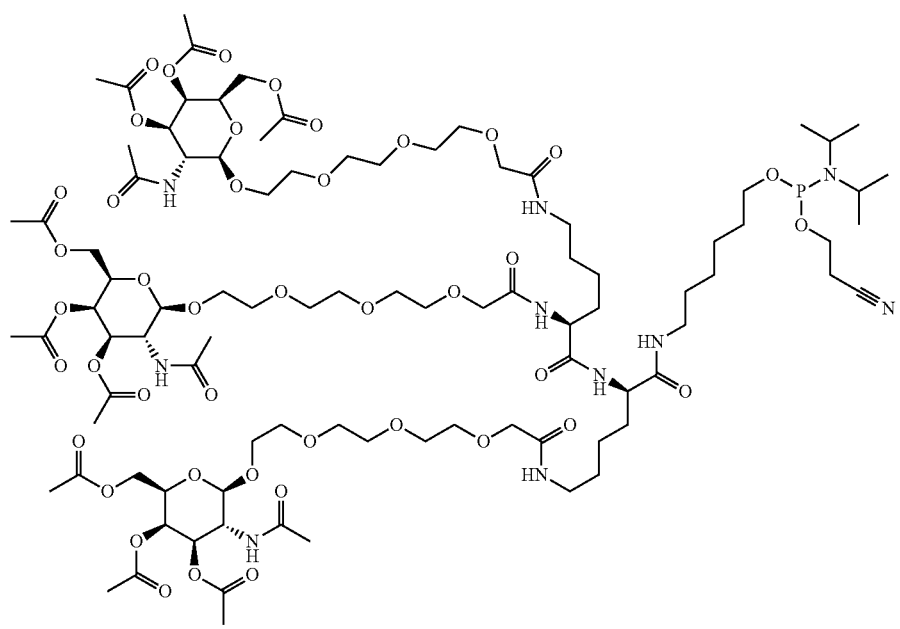
Ic

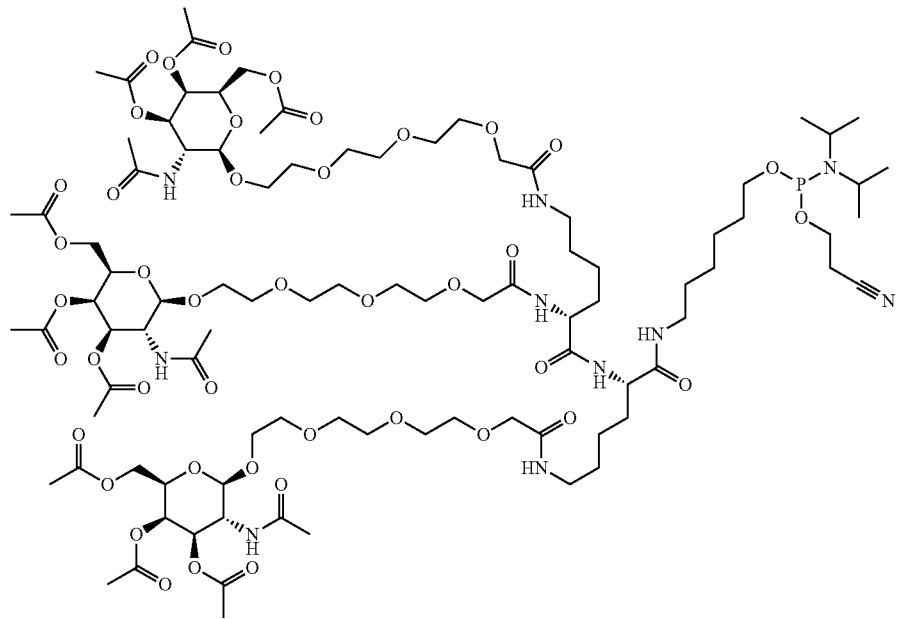
Id
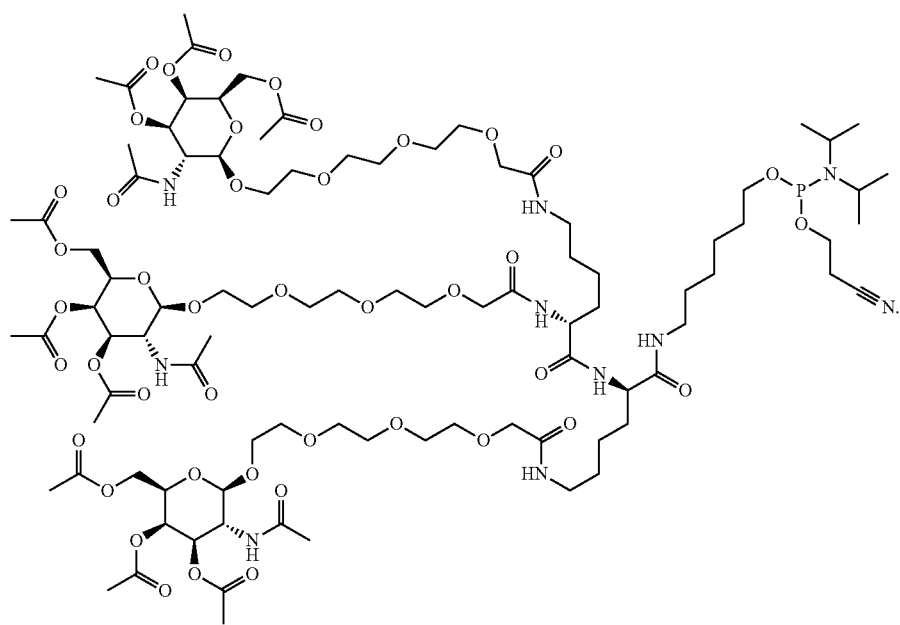
Ie

8. The process of claim 1, wherein the compound of formula II is prepared by:
a1) coupling a lysine compound of formula V

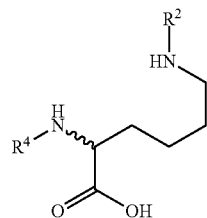

V wherein $R^2$ and $R^4$ are amino protecting groups;
with an amine of the formula VI

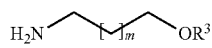

VI wherein $R^3$ and m are as above;
to form the carboxamide of formula VII;

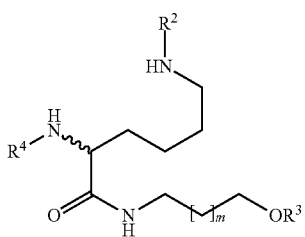

VII wherein $R^2$, $R^3$, $R^4$ and m are as above; and
b1) removing the amino protecting $R^4$ to form the amine of formula VIII

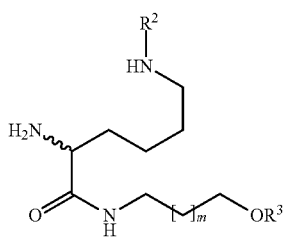

VIII wherein $R^2$, $R^3$ and m are as above;
c1) coupling the amine of formula VIII with an amino group protected lysine to form the dipeptide of formula IX

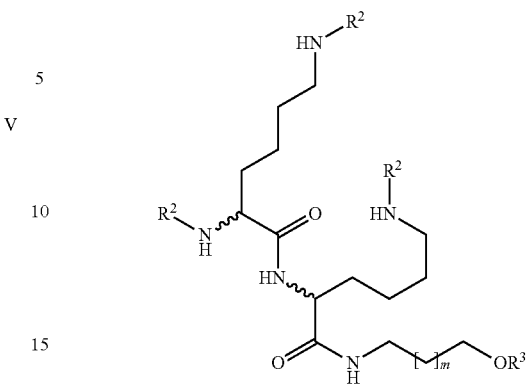

IX wherein $R^2$ and $R^3$ and m are as above; and
d1) removing the amino protecting groups $R^2$ to form the compound of formula II.

9. The process of claim 8, wherein the coupling steps a1) and c1) are performed in the presence of a peptide coupling agent, an amine base and an organic solvent.

10. The process of claim 9, wherein the peptide coupling agent is n-propylphosphonic acid anhydride, the amine base is a tertiary amine, the organic solvent is a polar aprotic solvent and the reaction temperature is selected from 20° C. to 70° C.

11. The process of claim 8, wherein $R^4$ is an amino protecting group cleavable under basic conditions, preferably FMOC.

12. The process of claim 11, wherein the basic conditions involve the treatment with a secondary aliphatic amine, preferably diethyl amine in the presence of an organic solvent.

13. The process of claim 8, wherein the amino protecting group $R^2$ is tert-butyloxycarbonyl.

14. The process of claim 8, wherein in step d1) the amino protecting group $R^2$ is removed under acidic conditions and a tri-ammonium salt of the dipeptide of formula IX with the respective acid is formed.

15. The process of claim 14, wherein the acid is a sulfonic acid, preferably methanesulfonic acid.

16. The process of claim 1, wherein the coupling of the compound of formula II with the GalNAc moiety of the formula III in step a) is performed in the presence of a peptide coupling agent, an amine base and an organic solvent.

17. The process of claim 16, wherein the peptide coupling agent is n-propylphosphonic acid anhydride, the amine base is a tertiary amine, the organic solvent is a polar aprotic solvent and the reaction temperature is selected from 20° C. to 70° C.

18. The process of claim 1, wherein the removing the hydroxyl protecting group $R^3$ to form the free alcohol in step b) is performed by way of a catalytic hydrogenation with hydrogen in the presence of a hydrogenation catalyst.

19. The process of claim 1, wherein the phosphoroamidating agent in step c) is selected from 2-cyanoethyl-N,N-di-(2-propyl) chlorophosphoroamidite or from 2-Cyanoethyl-N,N,N',N'-tetra (2-propyl)phosphorodiamidite.

20. The process of claim 19, wherein the reaction in step c) is performed with 2-Cyanoethyl-N,N,N',N'-tetra (2-propyl)phosphorodiamidite in the presence of an acidic ammonium salt of a secondary amine and a polar aprotic solvent at a reaction temperature between −20° C. and 50° C.

21. A process for the preparation of GalNAc-cluster oligonucleotide conjugates comprising a GalNac moiety as a single epimer, the process comprising the steps of:
  a) preparing a GalNAc phosphoramidite epimer of formula I according to the process of claim 1;
  b) contacting the GalNAc phosphoramidite epimer of formula I in a solid phase oligonucleotide synthesis together with a nucleoside building block and a solid support, in a sequence to form the GalNAc-cluster oligonucleotide conjugate bound to the solid support; and
  c) cleaving the GalNAc-cluster oligonucleotide conjugate from the solid phase support and fully deprotecting the GalNAc-cluster oligonucleotide conjugate.

* * * * *

SEQUENCE LISTING

<160> NUMBER OF SEQ ID NOS: 4

<210> SEQ ID NO 1
<211> LENGTH: 15
<212> TYPE: DNA
<213> ORGANISM: Oligonucleotide

<400> SEQUENCE: 1
cagcgtaaag agagg                                                      15

<210> SEQ ID NO 2
<211> LENGTH: 19
<212> TYPE: DNA
<213> ORGANISM: Oligonucleotide

```
<400> SEQUENCE: 2
cacctattta acatcagac                                            19

<210> SEQ ID NO 3
<211> LENGTH: 18
<212> TYPE: DNA
<213> ORGANISM: Oligonucleotide

<400> SEQUENCE: 3
catcaacttt cacttcag                                             18

<210> SEQ ID NO 4
<211> LENGTH: 16
<212> TYPE: DNA
<213> ORGANISM: Oligonucleotide

<400> SEQUENCE: 4
aatgctacaa acccca                                               16
```